United States Patent
Lee et al.

(10) Patent No.: US 10,497,873 B2
(45) Date of Patent: Dec. 3, 2019

(54) DISPLAY PANEL MANUFACTURING SYSTEM AND METHOD OF MANUFACTURING A DISPLAY PANEL USING THE SAME

(71) Applicant: Samsung Display Co., Ltd., Yongin-si (KR)

(72) Inventors: Byungchul Lee, Hwaseong-si (KR); Heungcheol Jeong, Hwaseong-si (KR); Myungsoo Huh, Suwon-si (KR); Jongsung Kim, Cheonan-si (KR); Byoung-hoon Choi, Hwaseong-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 15/996,531

(22) Filed: Jun. 4, 2018

(65) Prior Publication Data

US 2019/0103559 A1    Apr. 4, 2019

(30) Foreign Application Priority Data

Sep. 29, 2017    (KR) ........................ 10-2017-0128084

(51) Int. Cl.
  *H01L 21/00* (2006.01)
  *H01L 51/00* (2006.01)
  (Continued)

(52) U.S. Cl.
  CPC ........ *H01L 51/0012* (2013.01); *B41J 2/2135* (2013.01); *B41J 2/2146* (2013.01);
  (Continued)

(58) Field of Classification Search
  CPC .... H01L 51/0012; H01L 51/56; B41J 2/2135; B41J 2/2146; B41J 25/001; G01B 11/272; G01N 21/956
  See application file for complete search history.

(56) References Cited

U.S. PATENT DOCUMENTS 8,529,013 B2    9/2013  Watt et al.
9,050,795 B2 *  6/2015  Ueshima ................... B41J 2/12
(Continued)

FOREIGN PATENT DOCUMENTS

| JP | 2009-006212 | 1/2009 |
| KR | 10-2017-0027812 | 3/2017 |
| KR | 10-0781997 | 12/2017 |

*Primary Examiner* — Richard A Booth
(74) *Attorney, Agent, or Firm* — H.C. Park & Associates, PLC

(57) ABSTRACT

A display panel manufacturing system includes a substrate providing module configured to provide a substrate including an active region on which thin-film transistors are disposed, and a peripheral region adjacent to the active region, a test substrate providing module configured to provide a test substrate, an organic film forming module configured to form an ink pattern on each of the substrate and the test substrate, the organic film forming module including a plurality of heads, each of which is configured to drop an ink, an offset inspection module configured to inspect the ink pattern on the substrate, a pattern inspection module configured to inspect the ink pattern on the test substrate, and a droplet inspection module configured to inspect an ink, which is dropped from a head selected from the heads.

11 Claims, 20 Drawing Sheets

(51) Int. Cl.
    *G01B 11/27*     (2006.01)
    *G01N 21/956*     (2006.01)
    *H01L 51/56*     (2006.01)
    *B41J 2/21*     (2006.01)
    *B41J 25/00*     (2006.01)
    *H01L 27/32*     (2006.01)
    *B41J 2/01*     (2006.01)

(52) U.S. Cl.
    CPC ........... *B41J 25/001* (2013.01); *G01B 11/272* (2013.01); *G01N 21/956* (2013.01); *H01L 51/56* (2013.01); *B41J 2/01* (2013.01); *B41J 25/003* (2013.01); *G01B 2210/56* (2013.01); *H01L 27/3244* (2013.01); *H01L 51/0005* (2013.01)

(56) References Cited

U.S. PATENT DOCUMENTS

| | | |
|---|---|---|
| 9,120,107 B1 | 9/2015 | Sauter, Jr. |
| 9,537,119 B2 | 1/2017 | Harjee et al. |
| 10,099,497 B2 * | 10/2018 | Nagashima ................ B41J 2/01 |
| 10,180,623 B2 * | 1/2019 | Wakamatsu ........... B41J 2/2135 |
| 2009/0251504 A1 | 10/2009 | White |

\* cited by examiner

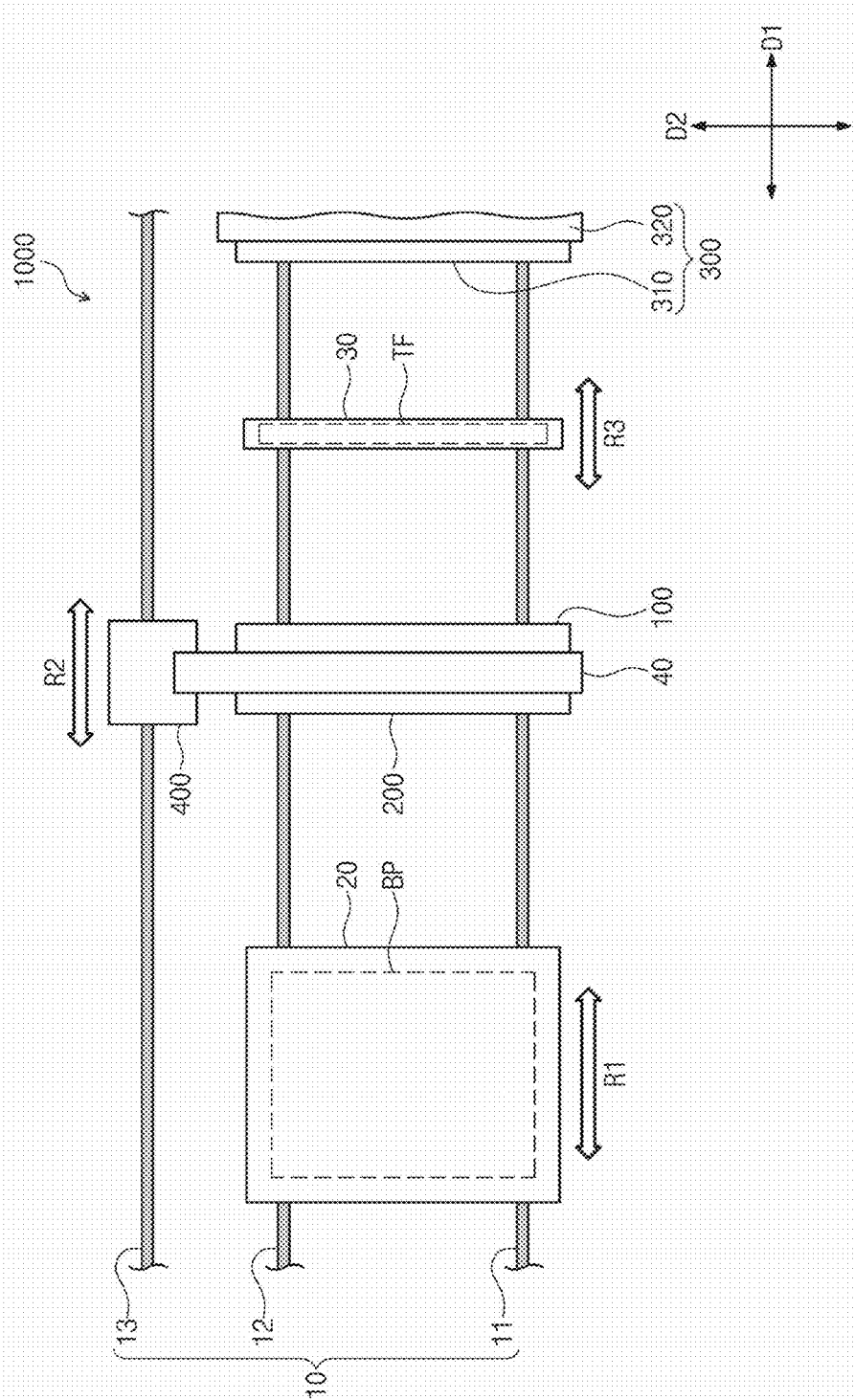

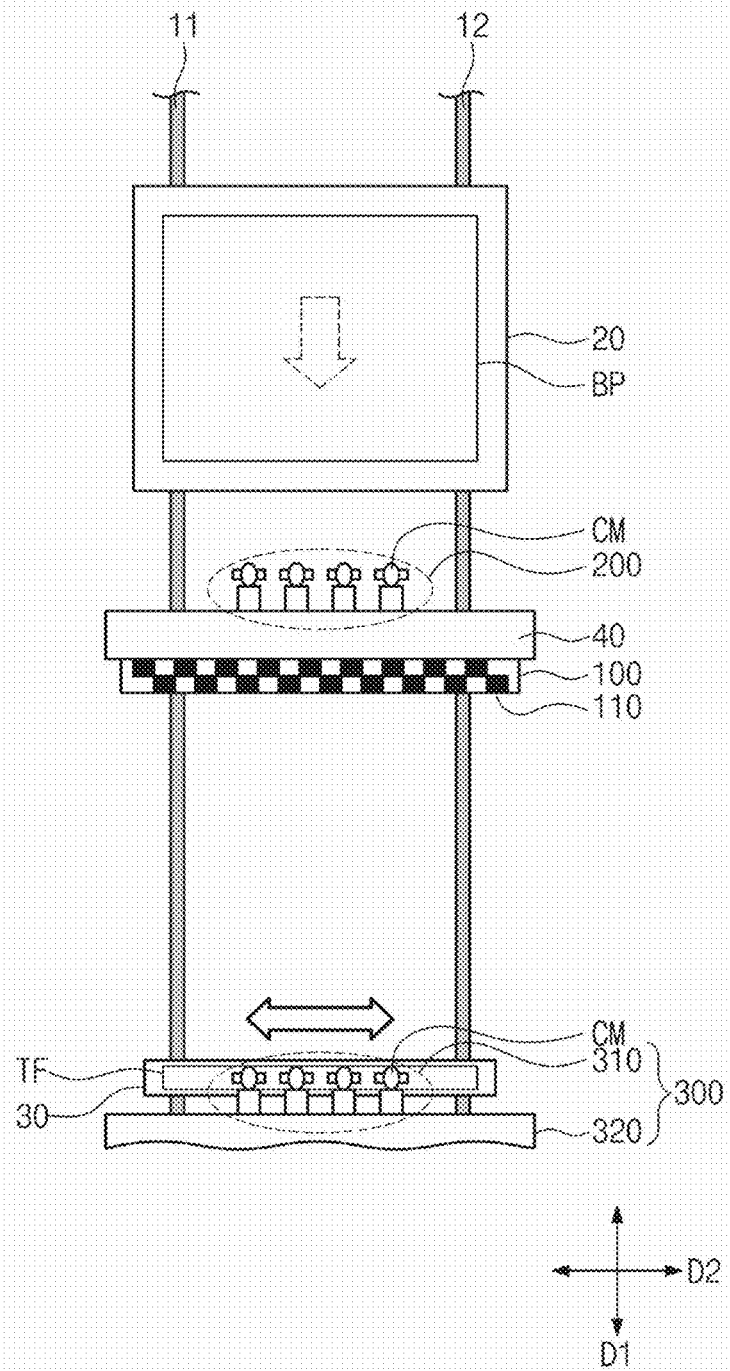

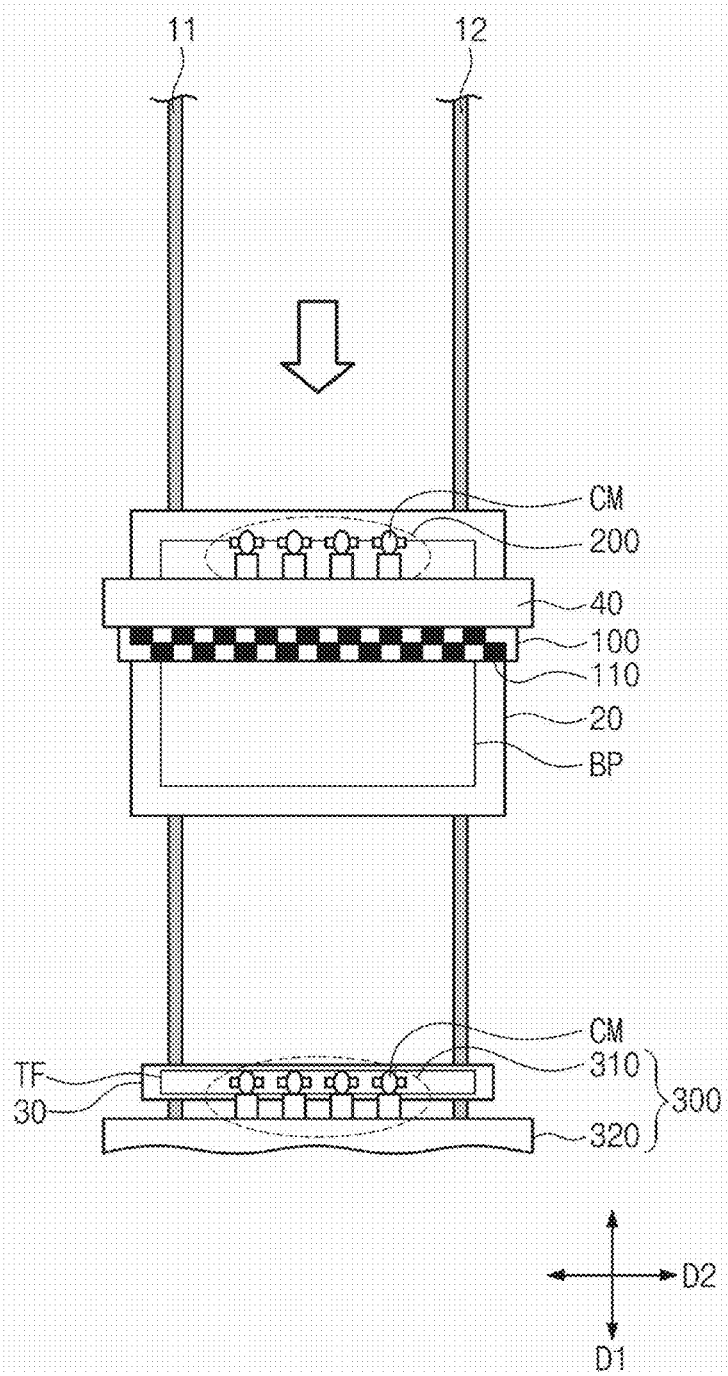

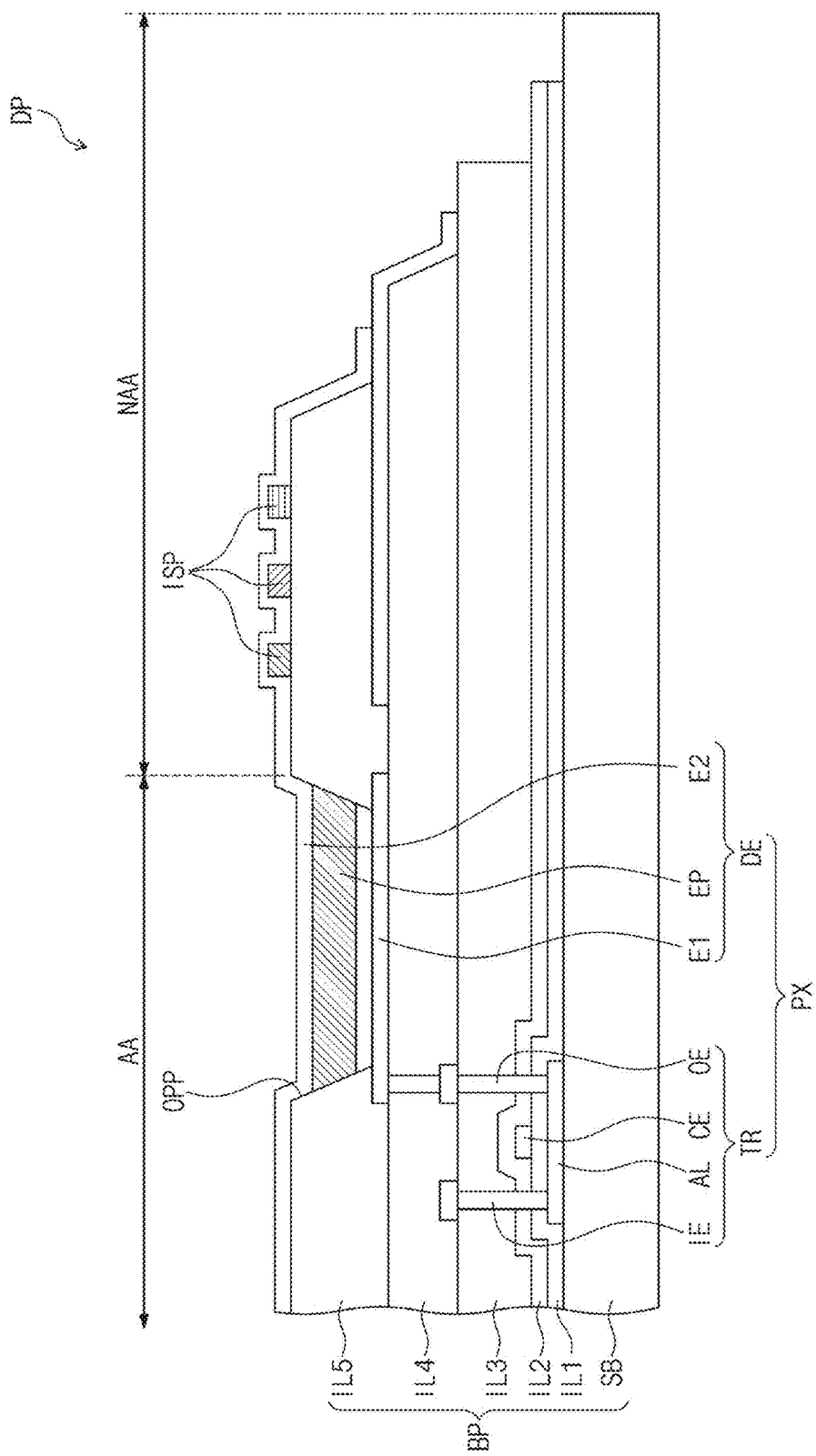

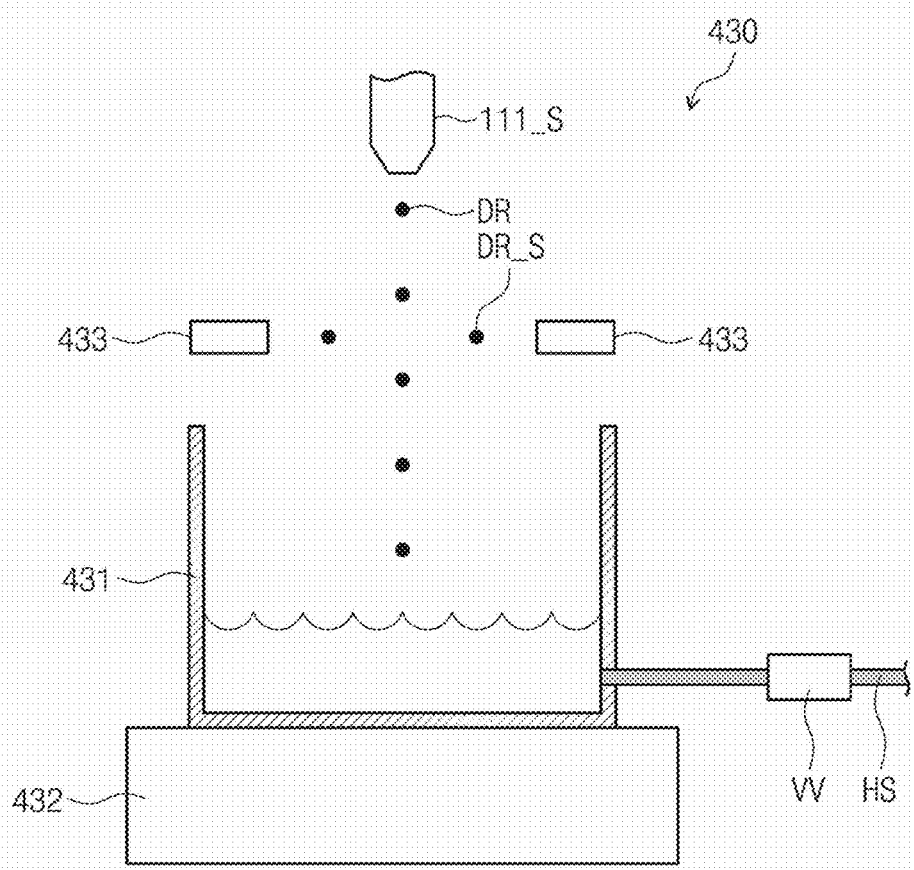

DISPLAY PANEL MANUFACTURING SYSTEM AND METHOD OF MANUFACTURING A DISPLAY PANEL USING THE SAME

CROSS-REFERENCE TO RELATED APPLICATIONS

This application claims priority from and the benefit of Korean Patent Application No. 10-2017-0128084, filed on Sep. 29, 2017, which is hereby incorporated by reference for all purposes as if fully set forth herein.

BACKGROUND

Field

Exemplary embodiments/implementations of the invention relate generally to a display panel manufacturing system and a method of manufacturing a display panel using the same, and more specifically, to a display panel manufacturing system including an inkjet device and a method of manufacturing a display panel using the same.

Discussion of the Background

A display panel is used to provide image information to a user. The display panel includes a plurality of pixels configured to display an image. For an organic light emitting display panel, each of the pixels includes an organic thin-film pattern containing a luminescent material.

The organic thin-film pattern is formed by various methods such as photolithographic and inkjet methods. For the inkjet method, an organic ink is dropped in an opening to form an ink pattern constituting the organic thin-film pattern.

In the case where the ink is dropped at an undesired position or is formed to incompletely or excessively fill the opening, the organic thin-film pattern may be formed to have defects. That is, quality of the organic thin-film pattern is highly dependent on whether the ink is dropped at a desired position.

The above information disclosed in this Background section is only for understanding of the background of the inventive concepts, and, therefore, it may contain information that does not constitute prior art.

SUMMARY

Some exemplary embodiments of the inventive concept provide a display panel manufacturing system, which is configured to perform an inspection process during an inkjet process.

Some exemplary embodiments provide a display panel manufacturing method, in which an inkjet process and an inspection process are simultaneously performed.

According to some exemplary embodiments, a display panel manufacturing system may include a substrate providing module configured to provide a substrate including an active region, on which thin-film transistors are disposed, and a peripheral region adjacent to the active region, a test substrate providing module configured to provide a test substrate, an organic film forming module configured to form an ink pattern on each of the substrate and the test substrate, the organic film forming module including a plurality of heads, each of which is configured to drop an ink, an offset inspection module configured to inspect the ink pattern on the substrate, a pattern inspection module configured to inspect the ink pattern on the test substrate, and a droplet inspection module configured to inspect an ink, which is dropped from a head selected from the heads.

In some exemplary embodiments, the organic film forming module, the offset inspection module, and the droplet inspection module may be configured to move together.

In some exemplary embodiments, the organic film forming module may be configured to form first ink patterns on the test substrate, and the pattern inspection module may be configured to inspect the first ink patterns and to adjust positions of the heads.

In some exemplary embodiments, the organic film forming module may be configured to form second ink patterns on the substrate, and the offset inspection module may be configured to inspect alignment accuracy between patterns, which are respectively formed on the active region and the peripheral region and are selected from the second ink patterns, and to adjust positions of the heads.

In some exemplary embodiments, the heads may be configured to move in a direction perpendicular to a motion direction of the substrate by the offset inspection module, and to move and rotate in a direction perpendicular to the motion direction of the substrate by the pattern inspection module.

In some exemplary embodiments, the selected head may be selected from the heads, when the first ink patterns or the second ink patterns are inspected.

In some exemplary embodiments, each of the heads may include a plurality of nozzles, and at least one of the nozzles of the selected head does not eject the ink or forms an ink pattern whose size may be different from that of a reference ink pattern.

In some exemplary embodiments, the droplet inspection module may include a laser irradiation device and an electronic balance device, and the laser irradiation device may be provided between the electronic balance device and the selected head and may be configured to inspect an ink, which is provided from the selected head to the electronic balance device.

In some exemplary embodiments, the droplet inspection module may further include a filter, the laser irradiation device includes a laser irradiation part, which is configured to irradiate the ink with a laser beam, and a laser receiving part, which is configured to receive a laser beam emitted from the ink, and the filter may be configured to control an intensity of a laser beam, which is incident from the laser irradiation part, and to control directivity of a laser beam, which is emitted from the ink.

In some exemplary embodiments, the filter may include a diffraction slit.

In some exemplary embodiments, the droplet inspection module further includes an ink suction device, and the ink suction device may be placed between the electronic balance device and the selected head and may be used to suction an ink to be leaked to an outside of the electronic balance device.

According to some exemplary embodiments of the inventive concept, a method of manufacturing a display panel nu providing a substrate, forming at least one ink pattern on the substrate to form an organic pattern, and a pattern inspection step of inspecting alignment accuracy of the ink pattern, an offset inspection step of inspecting alignment accuracy between the ink pattern and the substrate, and a droplet inspection step of inspecting an ink, which is dropped on the substrate to form the ink pattern, the step of inspecting the ink pattern may be performed during the step of forming the organic pattern.

In some exemplary embodiments, the ink pattern may be formed by dropping an ink from a head to the substrate, and the ink pattern inspection step may be performed to adjust a position of the head.

In some exemplary embodiments, the pattern inspection step may be performed to change a position of the head through a translational motion and a rotational motion on a plan view, and the offset inspection step may be performed to change the position of the head through a translational motion on a plan view.

In some exemplary embodiments, the head includes a plurality of heads, each of which may be independently controlled.

In some exemplary embodiments, the head includes a plurality of heads, and the droplet inspection step may be performed to inspect an ink dropped from a single head, which may be selected from the heads.

In some exemplary embodiments, the droplet inspection step may be performed to adjust an amount of ink dropped from the selected single head, and the selected head may be selected in at least one of the pattern inspection step and the offset inspection step.

In some exemplary embodiments, the droplet inspection step may be performed to replace the selected single head with a new head.

In some exemplary embodiments, the droplet inspection step may be performed using a laser beam.

In some exemplary embodiments, the droplet inspection step may be performed using an electronic balance device.

Additional features of the inventive concepts will be set forth in the description which follows, and in part will be apparent from the description, or may be learned by practice of the inventive concepts.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

FIG. 2 is a plan view illustrating a display panel manufacturing system according to some exemplary embodiments.

FIGS. 3A, 3B, 3C, 3D, and 3E are plan views illustrating a display panel manufacturing system according to some exemplary embodiments.

FIG. 5 is a cross-sectional view illustrating a portion of the substrate shown in FIG. 4.

FIGS. 14A and 14B are cross-sectional views, each illustrating a portion of a display panel manufacturing system according to some exemplary embodiments.

Figure 1:
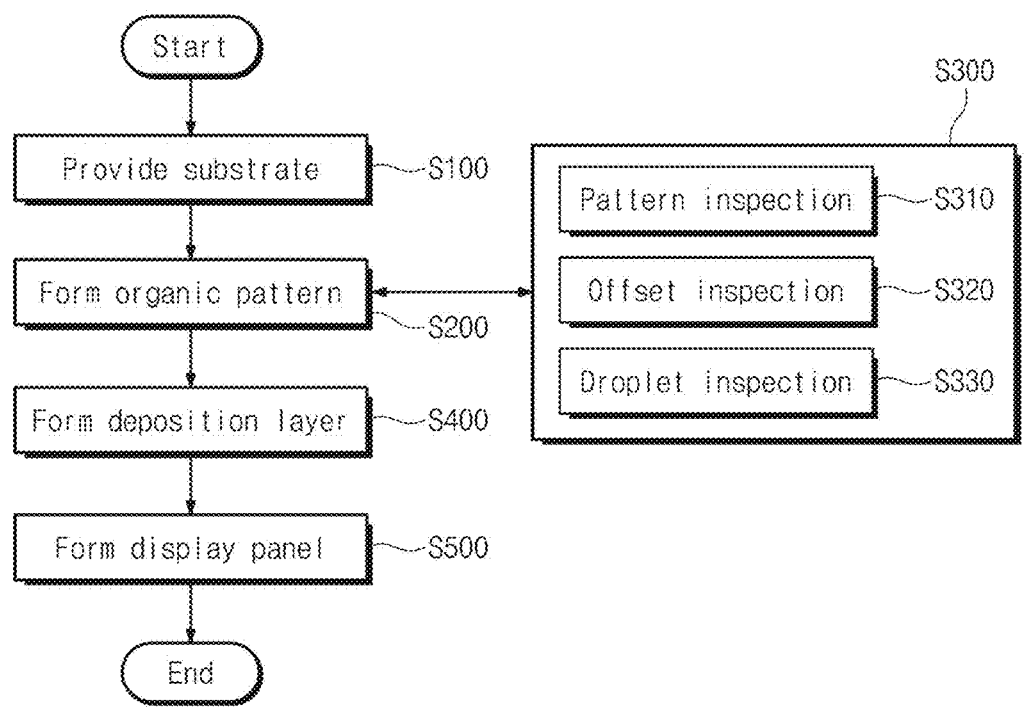
FIG. 1 is a flow chart illustrating a method of manufacturing a display panel according to some exemplary embodiments.

It should be noted that these figures are intended to illustrate the general characteristics of methods, structure and/or materials utilized in certain example exemplary embodiments and to supplement the written description provided below. These drawings are not, however, to scale and may not precisely reflect the precise structural or performance characteristics of any given exemplary embodiment, and should not be interpreted as defining or limiting the range of values or properties encompassed by example exemplary embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various exemplary embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "below," "lower," "upper," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular exemplary embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Exemplary embodiments of the inventive concepts will now be described more fully with reference to the accompanying drawings, in which exemplary embodiments are shown.

FIG. 1 is a flow chart illustrating a method of manufacturing a display panel according to some exemplary embodiments. FIG. 2 is a plan view illustrating a display panel manufacturing system according to some exemplary embodiments. Hereinafter, some exemplary embodiments will be described with reference to FIGS. 1 and 2.

As shown in FIG. 1, a method of manufacturing a display panel may include a substrate providing step S100, an organic pattern forming step S200, an inspection step S300, a deposition layer forming step S400, and a display panel forming step S500. The method of manufacturing a display panel may be performed using a display panel manufacturing system 1000.

The substrate providing step S100 may include inputting a substrate BP to the display panel manufacturing system 1000. In the display panel manufacturing system 1000, the organic pattern forming step S200 and the inspection step S300 may be performed. Thus, the substrate BP, on which all previous processes, except for a process of forming an organic pattern, have been performed, may be provided in the substrate providing step S100. For example, the substrate BP, on which a process of forming a thin-film transistor has been performed, may be provided in the substrate providing step S100. This will be described in more detail below.

The organic pattern forming step S200 may include dropping ink, which is formed of or includes an organic material, onto the substrate BP to form an organic thin-film pattern on the substrate BP. In some exemplary embodiments, a plurality of organic patterns may be formed to correspond to a plurality of pixels, and each of them may include a light-emitting pattern to be described below. This will be described in more detail below.

The inspection step S300 may include inspecting the organic pattern and the dropping ink. In the present exemplary embodiment, the inspection step S300 may be performed simultaneously with the organic pattern forming step S200. Data, which are produced in the inspection step S300, may be used for the organic pattern forming step S200, and vice versa. The organic pattern forming step S200 may be monitored in real time by the inspection step S300, and this may make it possible to improve quality of the organic pattern.

The deposition layer forming step S400 may include forming at least one layer using a deposition process. The deposition layer forming step S400 may be performed on the substrate BP, on which the organic pattern is formed. The deposition layer may be formed to encapsulate and protect the organic pattern.

The display panel forming step S500 may include all steps, which are performed between the deposition layer forming step S400 and a packing step. The display panel forming step S500 may further include forming a color filter or a touch unit on the deposition layer. In addition, the display panel forming step S500 may further include a final inspection step, such as an electrical test step or an appearance inspection step. The display panel, which is formed by the display panel forming step S500, may be delivered to other system and then may be coupled to a circuit board and so forth.

Referring to FIG. 2, the display panel manufacturing system 1000 may include an organic film forming module 100, an offset inspection module 200, a pattern inspection module 300, and a droplet inspection module 400. As described above, the organic pattern forming step S200 and the inspection step S300 of FIG. 1 may be performed by the display panel manufacturing system 1000.

The organic film forming module 100, the offset inspection module 200, the pattern inspection module 300, and the droplet inspection module 400 may be controlled by a single control unit (not shown). In some exemplary embodiments, the display panel manufacturing system 1000 may further include a rail 10, a substrate provider 20, a test substrate provider 30, and a gantry part 40. Here, the rail 10 may be used as a pathway of the organic film forming module 100, the offset inspection module 200, the pattern inspection module 300, and the droplet inspection module 400, and the substrate provider 20 may be configured to provide the substrate BP along the rail 10. The test substrate provider 30 may be configured to provide a test substrate TF along the rail 10, and the gantry part 40 may be configured to connect the organic film forming module 100, the offset inspection module 200, and the pattern inspection module 300.

The rail 10 may include first, second and third rails 11, 12, 13, which extend in a first direction D1 and are arranged to be spaced apart from each other in a second direction D2 crossing the first direction D1. The substrate provider 20 and the test substrate provider 30 may be provided to be movable in an extension direction of the rail 10. In the display panel manufacturing system 1000 according to some exemplary embodiments, a moving direction R1 of the substrate BP may be defined as the first direction D1. In the present specification, one direction will be used to indicate two opposite directions on the same straight line.

The substrate provider 20 may be coupled to the first rail 11 and the second rail 12 and may be configured to move in the first direction D1. The substrate provider 20 may be used to provide the substrate BP to the organic film forming module 100 and the offset inspection module 200. The substrate BP to be provided on the substrate provider 20 is illustrated by a dotted line, for convenience in description.

The test substrate provider 30 may be coupled to the first rail 11 and the second rail 12 and may be configured to move in the first direction D1. The test substrate provider 30 may be used to provide the test substrate TF to the pattern inspection module 300 and the droplet inspection module 400. The test substrate TF to be provided on the test substrate provider 30 is illustrated by a dotted line, for convenience in description.

The gantry part 40 may extend in the second direction D2 and may be used to connect the organic film forming module 100, the offset inspection module 200, and the droplet inspection module 400. Thus, motions R2 of the organic film forming module 100, the offset inspection module 200, and the droplet inspection module 400 may be simultaneously executed in the first direction D1.

The organic film forming module 100 may be configured to drop ink, which is formed of or includes an organic material, onto the substrate BP or the test substrate TF to form an organic pattern. A plurality of organic patterns may be overlapped to each other to form an organic film. The organic film forming module 100 may include an inkjet device. For example, although not shown, the organic film forming module 100 may include a plurality of heads. Each of the heads may include a plurality of nozzles, through which the ink is ejected. Positions of the heads may be independently controlled, within the organic film forming module 100. This will be described in more detail below.

The offset inspection module 200 may be used to inspect an organic pattern formed on the substrate BP. For example, the offset inspection module 200 may inspect a position of the organic pattern on the substrate BP to produce offset inspection result data. The offset inspection result data may be shared with the organic film forming module 100 and the substrate provider 20 and may affect alignment between the heads of the organic film forming module 100 and the substrate BP. The heads of the organic film forming module 100 may be moved and aligned in the second direction D2, based on the offset inspection result data, and the substrate BP may be moved and aligned in the first direction D1. Accordingly, the organic pattern may be stably formed at a desired position of the substrate BP, using the organic film forming module 100.

The pattern inspection module 300 may be used to inspect an organic pattern formed on the test substrate TF. The pattern inspection module 300 may inspect alignment accuracy, size, and presence/absence of the organic pattern formed on the test substrate TF to produce pattern inspection result data. The pattern inspection result data may be shaped by the organic film forming module 100 and may affect positional alignment between the heads of the organic film forming module 100. In addition, the pattern inspection result data may be shared with the droplet inspection module 400 and may be used to control an amount of the ink to be dropped through the head of the organic film forming module 100.

The pattern inspection module 300 may be coupled to the first rail 11 and the second rail 12 and may be moved or fixed in the first direction D1. The test substrate provider 30 may be configured to reciprocally move between the organic film forming module 100 and the pattern inspection module 300 and to provide the test substrate TF to the organic film forming module 100 or the pattern inspection module 300.

The droplet inspection module 400 may be coupled to the third rail 13 and may be configured to be movable along the third rail 13 or in the first direction D1. The droplet inspection module 400 may be mechanically coupled to the organic film forming module 100 and the offset inspection module 200 by the gantry part 40. Accordingly, even when the droplet inspection module 400 and the organic film forming module 100 are being moved along different rails, the motion of the droplet inspection module 400 may be controlled to be parallel to the motion R2 of the organic film forming module 100.

The droplet inspection module 400 may be configured to inspect ink, which is dropped through a head selected from the heads of the organic film forming module 100. The selected head of the organic film forming module 100 may be moved or provided to the droplet inspection module 400 through the gantry part 40.

The droplet inspection module 400 may be configured to inspect the selected head of the organic film forming module 100 to produce droplet inspection result data. If the inspection of the head using the droplet inspection module 400 is finished, a step of adjusting an amount of ink to be dropped through the selected head may be performed, based on the droplet inspection result data, and then may be moved to the organic film forming module 100 or may be replaced with other head. This will be described in more detail below.

In the display panel manufacturing system 1000 according to some exemplary embodiments, the offset inspection module 200, the pattern inspection module 300, and the droplet inspection module 400 may be systematically connected to the organic film forming module 100. For example, the offset inspection result data, the pattern inspection result data, and the droplet inspection result data may be shared in real time by the organic film forming module 100 and may be used for alignment and adjustment.

According to some exemplary embodiments, the display panel manufacturing system 1000 may be configured to simultaneously perform the organic pattern forming step S200 and the inspection step S300. The organic pattern forming step S200 may be performed to adjust the formation of an organic pattern, based on inspection result data transmitted in real time from the inspection step S300. As a result, it may be possible to realize a real-time monitoring of the organic pattern forming step S200, and this may make it possible to continuously maintain a process flow and to improve process efficiency (i.e., to reduce process time and cost) in a manufacturing process.

FIGS. 3A, 3B, 3C, 3D, and 3E are plan views illustrating a display panel manufacturing system according to some exemplary embodiments. In detail, each of FIGS. 3A, 3B, 3C, 3D, and 3E schematically illustrates configuration of the display panel manufacturing system 1000 in a pattern inspection step S310 or an offset inspection step S320.

As shown in FIGS. 3A, 3B, 3C, 3D, and 3E, the organic film forming module 100 may be provided at a side of the gantry part 40. The organic film forming module 100 may include a plurality of heads 110. For convenience in illustration, the heads 110 are painted in black. The heads 110 may be arranged in the second direction D2, but the arrangement may be variously changed. In the present exemplary embodiment, the heads 110 are illustrated to be alternately arranged in two columns in the first direction D1.

The offset inspection module 200 may be provided at an opposite side of the gantry part 40. The offset inspection module 200 may include at least on camera module CM. In some exemplary embodiments, a plurality of camera modules CM may be provided to be spaced apart from each other in the second direction D2.

The number of the camera module CM may be one or more, and in certain exemplary embodiments, at least one of the camera modules CM may be configured to be linearly movable in the second direction D2. Accordingly, the offset inspection module 200 may be used to inspect all regions of the substrate BP in the second direction D2 with ease.

The pattern inspection module 300 may include an imaging module 310 and a supporting module 320. The imaging module 310 may be fixed by the supporting module 320, and the supporting module 320 may be coupled to the rail 10 and may be used to move or fix the imaging module 310 in the first direction D1.

The imaging module 310 may include the camera module CM. The number of the camera module CM may be one or more, and in certain exemplary embodiments, at least one of the camera modules CM may be configured to be linearly movable in the second direction D2. Accordingly, the pattern inspection module 300 may be used to inspect all regions of the substrate BP in the second direction D2 with ease.

Hereinafter, some exemplary embodiments will be described with reference to FIGS. 3A, 3B, 3C, 3D, and 3E.

Figure 3A:
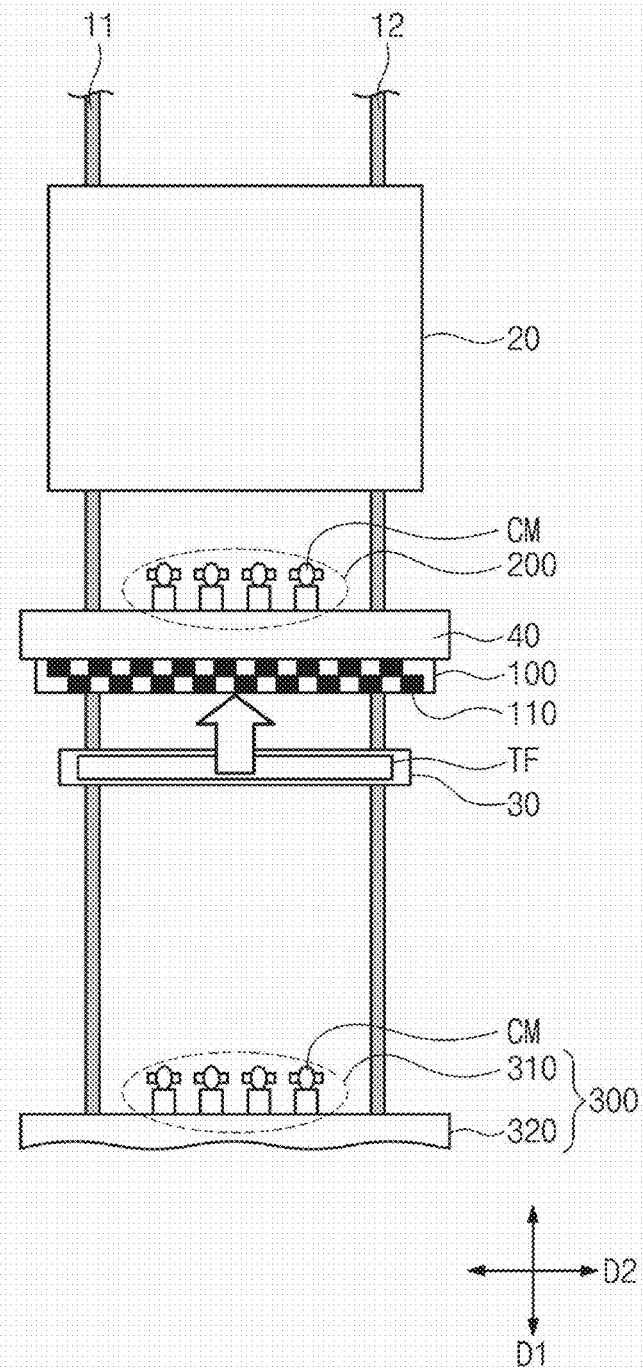

FIGS. 3A and 3B may correspond to the pattern inspection step S310 (e.g., see FIG. 1). In detail, referring to FIG. 3A, the pattern inspection step S310 may start to perform when the test substrate provider 30 moves toward the organic film forming module 100. The test substrate provider 30 may provide the test substrate TF to the organic film forming module 100. The organic film forming module 100 may be used to form an ink pattern (not shown) on the test substrate TF.

Next, as shown in FIG. 3B, the test substrate provider 30 may be moved in the first direction D1 to provide the test substrate TF to the pattern inspection module 300. The pattern inspection module 300 may inspect the ink pattern, which is formed on the test substrate TF, using the imaging module 310, to produce pattern inspection result data. The pattern inspection result data may be prepared to contain information on alignment accuracy, size, and presence/absence of the ink pattern.

The pattern inspection result data may be shared with the organic film forming module 100 and may be used to adjust positions of the heads 110. The adjustment of the positions of the heads 110, using the pattern inspection result data, may be performed through a translational motion in the second direction D2 and through a rotational motion of each of the heads 110.

Figure 3D:
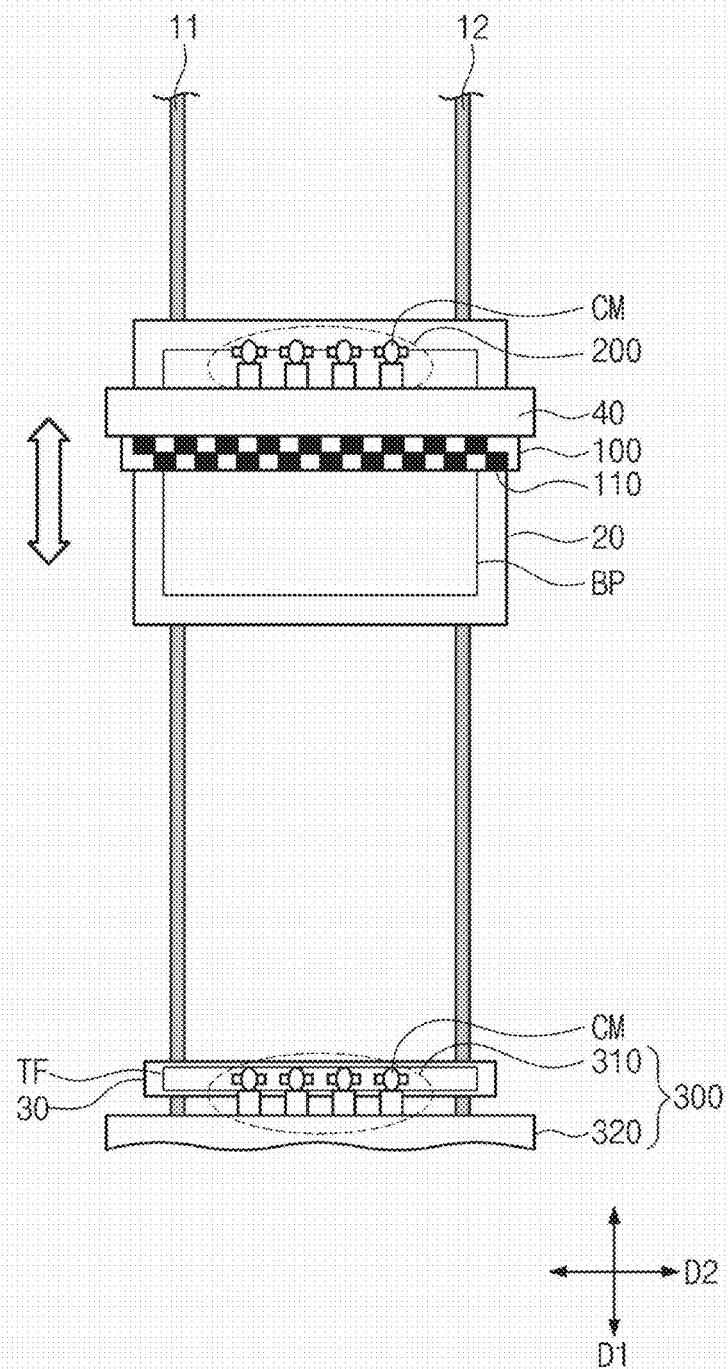
Figure 3E:
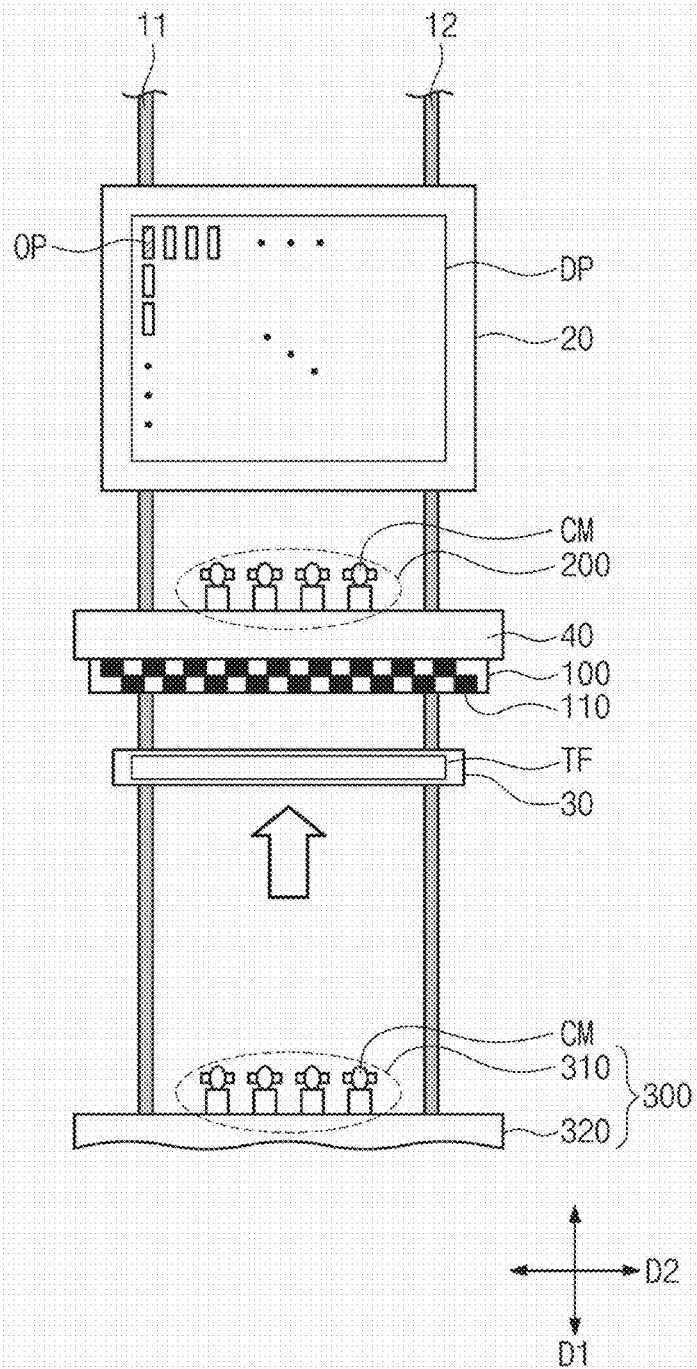

FIGS. 3C, 3D, and 3E may correspond to the offset inspection step S320 (e.g., see FIG. 1) and the organic pattern forming step S200. In detail, referring to FIG. 3C, the offset inspection step S320 may be performed to move the substrate provider 20 toward the organic film forming module 100. The substrate provider 20 may provide the substrate BP to the organic film forming module 100. The organic film forming module 100 may be used to form an ink pattern (not shown) on the substrate BP.

Thereafter, as shown in FIG. 3C, the substrate provider 20 may be moved in the first direction D1 or in a direction depicted by the arrow to provide the substrate BP to the offset inspection module 200. The offset inspection module 200 may inspect the ink pattern, which is formed on the substrate BP, using the camera module CM, to produce offset inspection result data. The offset inspection result data may be prepared to contain information on alignment accuracy between the ink pattern and the substrate BP. In addition, the offset inspection result data may be prepared to further contain information on size and presence/absence of the ink pattern.

The offset inspection result data may be shared with the organic film forming module 100 and may be used to adjust positions of the heads 110. The adjustment of the positions of the heads 110, using the offset inspection result data, may be performed through a translational motion in the second direction D2.

In some exemplary embodiments, the offset inspection result data may also be shared with the substrate provider 20 and may be used to adjust a position of the substrate BP. The adjustment of the position of the substrate BP, using the offset inspection result data, may be performed through a translational motion in the first direction D1.

As shown in FIGS. 3D and 3E, the substrate provider 20 may be reciprocally moved in the first direction D1 or in a direction depicted by the arrow. The adjustment of the positions of the heads 110 using the pattern inspection result and the offset inspection result may be performed in a real time manner. Owing to the reciprocal motion of the substrate provider 20, the substrate BP may be repeatedly provided to the organic film forming module 100. The ink pattern formed on the substrate BP by the organic film forming module 100 may be stacked to have a multi-layered structure or may be formed to cover the entire surface of the substrate BP, thereby forming an organic pattern OP. The organic pattern OP may correspond to a light-emitting pattern to be described below.

As shown in FIG. 3E, when the formation of the organic pattern OP is finished, a display panel DP may be transferred from the display panel manufacturing system 1000 to other system. In such other system, the deposition layer forming step S400 (e.g., see FIG. 1) may be performed on the display panel DP.

As shown in FIG. 3E, when the display panel DP is moved to the outside, the test substrate provider 30 may be moved in the arrow direction to provide the test substrate TF to the organic film forming module 100. In other words, the pattern inspection step S310 described with reference to FIG. 3A may be performed again. In the display panel manufacturing system 1000 according to some exemplary embodiments, the organic pattern forming step S200 and the inspection step S300 may be performed at substantially the same time through the afore-described process flow. Thus, it may be possible to reduce process time and cost in a process of manufacturing a display panel. In addition, since the process of forming the organic pattern is monitored in real time, it may be possible to improve reliability of the display panel DP.

Figure 4:
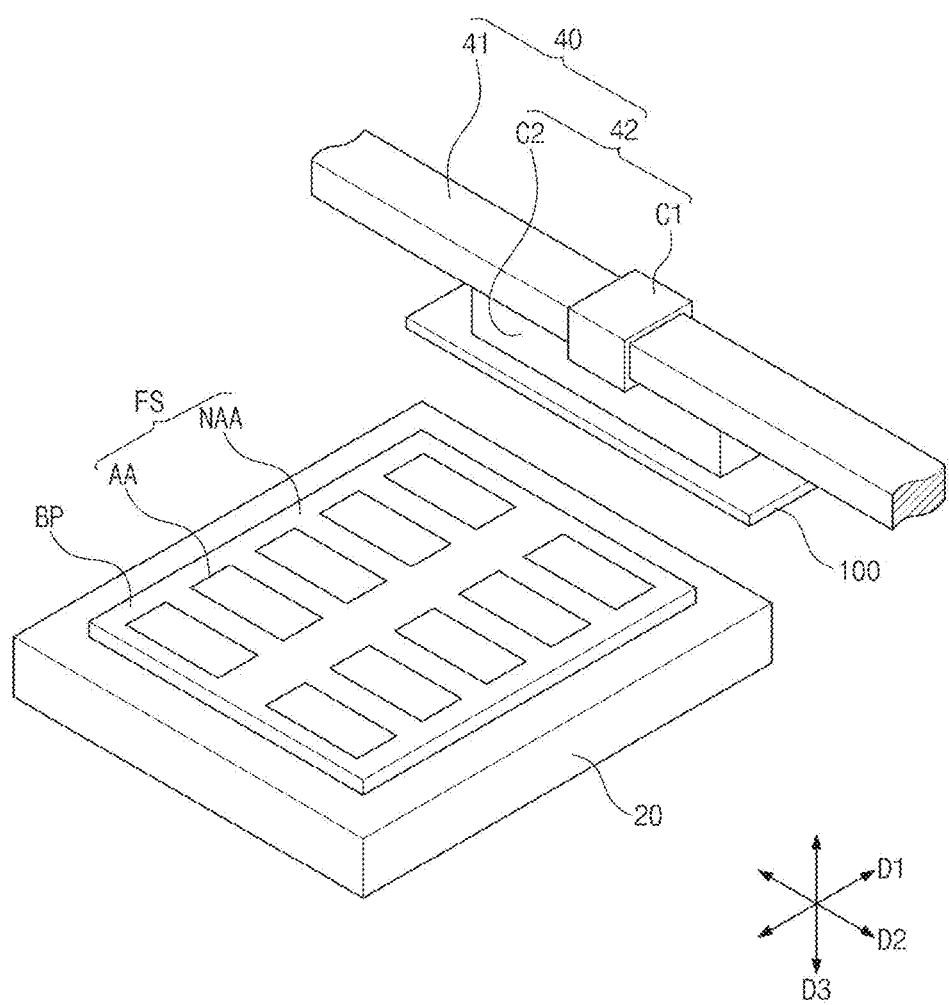
FIG. 4 is a perspective view illustrating a portion of a display panel manufacturing system according to some exemplary embodiments.

FIG. 4 is a perspective view illustrating a portion of a display panel manufacturing system according to some exemplary. FIG. 5 is a cross-sectional view illustrating a portion of the substrate shown in FIG. 4. Hereinafter, some exemplary embodiments will be described with reference to FIGS. 4 and 5. For concise description, an element previously described with reference to FIGS. 1, 2, 3A, 3B, 3C, 3D, and 3E may be identified by a similar or identical reference number without repeating an overlapping description thereof.

FIG. 4 illustrates a portion of the system connected to the organic film forming module 100. As shown in FIG. 4, the gantry part 40 may be mechanically or physically connected to the organic film forming module 100 provided on the substrate provider 20. The gantry part 40 may include a coupling unit 41 and a moving unit 42.

The coupling unit 41 may be a line shaped structure extending in the second direction D2. The coupling unit 41 may be provided to cross the first to third rails 11, 12, and 13 shown in FIG. 2. The coupling unit 41 may be configured to mechanically or physically couple the organic film forming module 100, the offset inspection module 200 (e.g., see FIG. 1), and the droplet inspection module 400 (e.g., see FIG. 2) to each other. In addition, the coupling unit 41 may be configured to electrically connect the organic film forming module 100, the offset inspection module 200, the pattern inspection module 300, and the droplet inspection module 400 to each other through signal lines (not shown).

The moving unit 42 may be provided to connect the coupling unit 41 to the organic film forming module 100. The moving unit 42 may include a first portion C1, which is provided to surround the coupling unit 41, and a second portion C2, which is connected to the first portion C1 and the organic film forming module 100. The first portion C1 may be coupled to the coupling unit 41 to be movable along the coupling unit 41. The moving unit 42 may be configured to allow the organic film forming module 100 to be easily moved along the coupling unit 41 and in the second direction D2.

For convenience in illustration, the organic film forming module 100 is illustrated to be coupled to a lower portion of the gantry part 40, but the inventive concept is not limited thereto. For example, the organic film forming module 100 may be provided at a side of the offset inspection module 200 and a side of the coupling unit 41, with the coupling unit 41 interposed therebetween.

The substrate BP, which is provided on the substrate provider 20 and adjacent to the organic film forming module 100, is schematically illustrated in FIG. 4. The substrate BP may have a front surface FS including an active region AA and a peripheral region NAA. The front surface FS may be a surface, on which an ink pattern (not shown) formed by the organic film forming module 100 is provided.

In some exemplary embodiments, a plurality of active regions AA may be provided. Thus, the substrate BP may correspond to a mother board. Each of the active region AA may correspond to a display region of a display panel. However, the inventive concept is not limited thereto, and for example, the substrate BP may be configured to have one active region AA.

FIG. 5 illustrates a cross-sectional view of the display panel DP. The display panel DP may include the substrate BP shown in FIG. 4. The display panel DP may correspond to the display panel DP shown in FIG. 3E.

As shown in FIG. 5, the display panel DP may include a base substrate SB, a pixel PX, a plurality of insulating layers IL1 IL2, IL3, IL4, and IL5, and an inspection pattern ISP. The insulating layers ILL IL2, IL3, IL4, and IL5 are sequentially stacked on the base substrate SB, as exemplarily shown in FIG. 5, but the inventive concept is not limited thereto.

The base substrate SB may have an insulating property. For example, the base substrate SB may be or include a glass substrate, a plastic substrate, a silicon substrate, an insulating film, or any combination thereof.

The pixel PX may be provided on the base substrate SB. The pixel PX may be provided in the active region AA. The pixel PX may include a thin-film transistor TR and a display element DE. The thin-film transistor TR may include a semiconductor pattern AL, a control electrode CE, an input electrode IE, and an output electrode OE.

The control electrode CE may be provided on the first insulating layer IL1 and may be spaced apart from the semiconductor pattern AL by the first insulating layer IL1 interposed therebetween. The control electrode CE may be provided to be overlapped with the semiconductor pattern AL, when viewed in a plan view. The input electrode IE and the output electrode OE may be provided on the third insulating layer IL3, and each of them may penetrate the first to third insulating layers ILL IL2, and IL3, thereby being coupled to the semiconductor pattern AL.

The display element DE may be an organic light emitting device. For example, the display element DE may include a first electrode E1, an organic pattern EP, and a second electrode E2. In the display element DE, depending on potential difference between the first electrode E1 and the second electrode E2, the organic pattern EP may be activated to emit light.

The first electrode E1 may be provided on the fourth insulating layer IL4 and may penetrate the fourth insulating layer IL4, thereby being coupled to the thin-film transistor TR. The second electrode E2 may be provided on the fifth insulating layer IL5. The second electrode E2 may be provided in the opening OPP, which is formed to penetrate the fifth insulating layer IL5, and may be spaced apart from the first electrode E1 by the organic pattern EP interposed therebetween.

The organic pattern EP may be provided between the first electrode E1 and the second electrode E2. The organic pattern EP may be provided in the opening OPP. The organic pattern EP may be formed of or include a luminescent material. Depending on potential difference between the first electrode E1 and the second electrode E2, excitons generating light may be produced in the organic pattern EP. The organic pattern EP may include a luminescent or light-emitting pattern.

Although not shown, the display element DE may further include an organic layer, which is provided between the organic pattern EP and the first electrode E1 and/or between the organic pattern EP and the second electrode E2. The organic layer may include a hole control layer and/or an electron control layer. The organic layer may be configured to improve light-emitting efficiency of the display element DE and to increase life of the display element DE.

In some exemplary embodiments, the inspection pattern ISP may be provided on the peripheral region NAA. The inspection pattern ISP may be provided between the fifth insulating layer IL5 and the second electrode E2. The inspection pattern ISP may be formed of or include the same material as the organic pattern EP. For example, in the case where, as shown in FIG. 5, a plurality of inspection patterns ISP are provided, one of them may be formed of or include the same material as the organic pattern EP adjacent thereto, and another may be formed of or include the same material as other organic pattern EP in the active region AA.

The ink pattern formed by the organic film forming module 100 may include the organic pattern EP and the inspection pattern ISP. The organic pattern EP may be formed on the active region AA, and the inspection pattern ISP may be formed on the peripheral region NAA.

The organic pattern EP may be formed by stacking a plurality of ink patterns. That is, the substrate BP may have a structure, in which the organic pattern EP of the display panel DP is not formed yet (i.e., having the fifth insulating layer IL5, in which the opening OPP formed). Thus, the substrate BP shown in FIG. 4 may be configured to include the base substrate SB, the thin-film transistor TR, the first electrode E1, and the first to the fifth insulating layers IL1 to IL5.

To form the organic pattern EP, it is necessary to stably drop the ink patterns in the opening OPP. Alignment accuracy between the inspection pattern ISP and the opening OPP may be used as alignment accuracy between the ink pattern and the substrate, in the offset inspection step S320.

An amount of ink to be dropped through the organic film forming module 100 may affect a thickness of the organic pattern EP. If the amount of ink to be dropped through the organic film forming module 100 is reduced, the opening OPP may be incompletely filled with the organic pattern EP, and if the amount of ink to be dropped through the organic film forming module 100 is increased, the organic pattern EP may be formed on a neighboring region beyond the opening OPP; that is, there may be an over-filling issue.

In some exemplary embodiments, the pattern inspection step S310, the offset inspection step S320, and a droplet inspection step S330 may be performed simultaneously with the organic pattern forming step S200, and in this case, the organic pattern EP may be stably formed at a predetermined position and to a desired thickness. Accordingly, it may be possible to improve reliability of the display panel DP and to reduce process cost in a process of manufacturing the display panel DP.

Figure 6A:
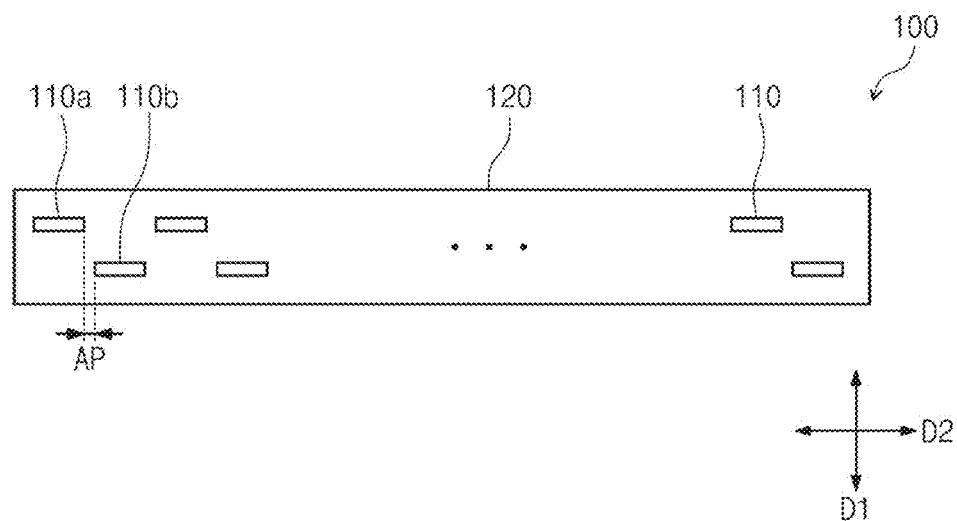
FIGS. 6A, 6B, 6C, and 6D are plan views, each illustrating a portion of a display panel manufacturing system according to some exemplary embodiments.
Figure 6B:
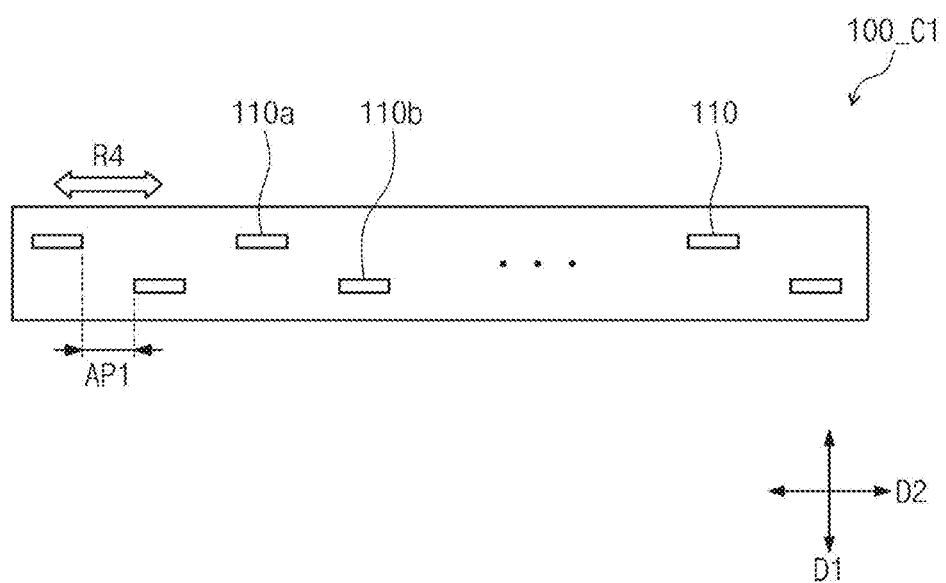
Figure 6C:
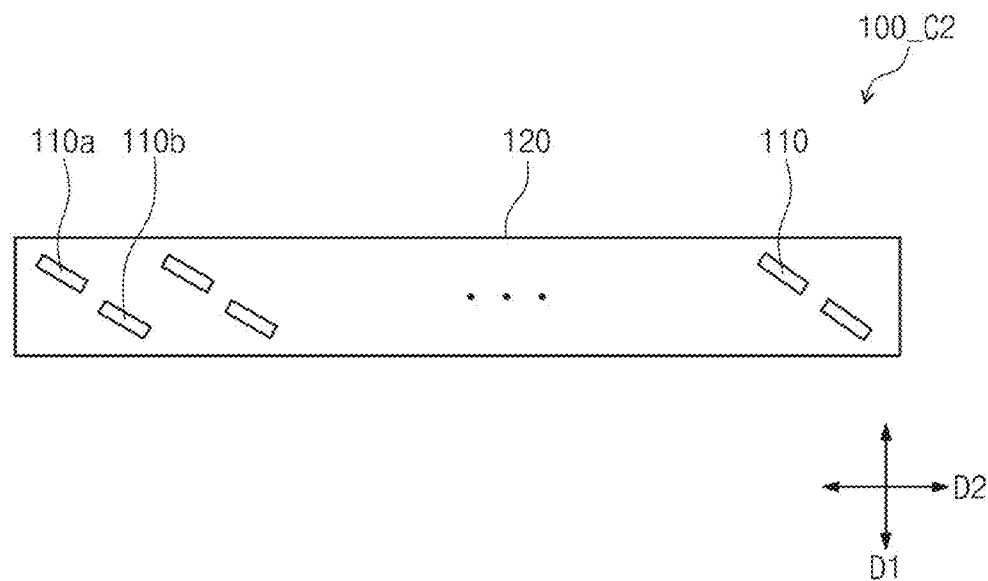
Figure 6D:
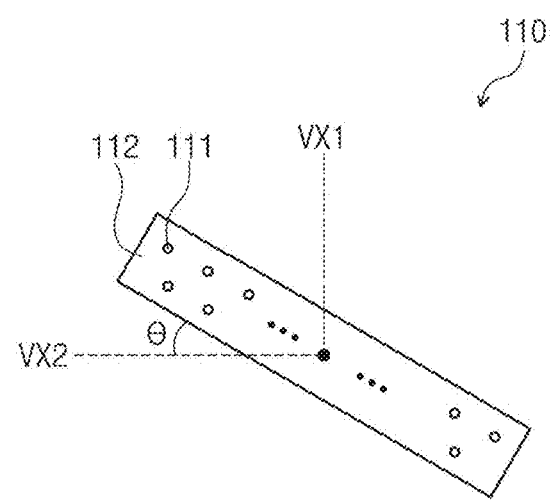
Figure 7A:
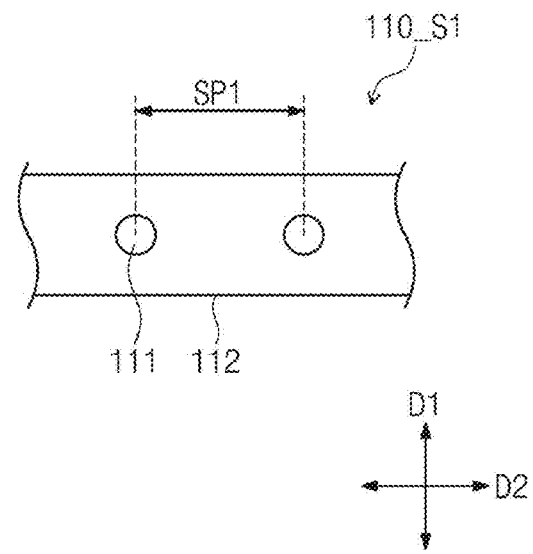
FIGS. 7A and 7B are plan views, each illustrating a portion of a display panel manufacturing system according to some exemplary embodiments.
Figure 7B:
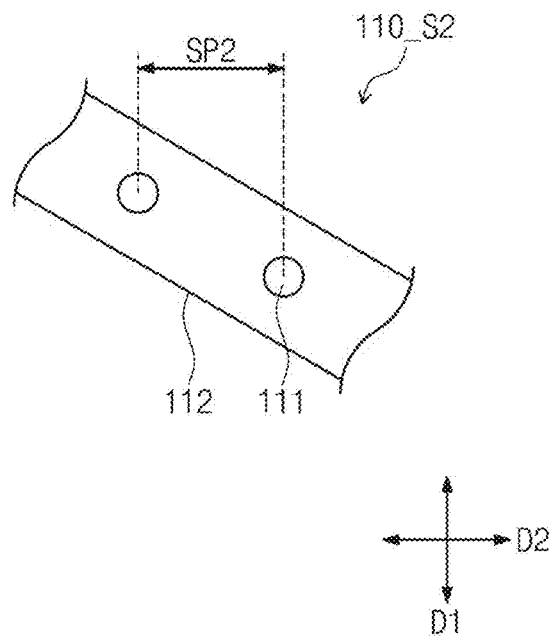

FIGS. 6A, 6B, 6C, and 6D are plan views, each illustrating a portion of a display panel manufacturing system according to some exemplary embodiments. FIGS. 7A and 7B are plan views, each illustrating a portion of a display panel manufacturing system according to some exemplary embodiments. FIG. 6A illustrates a plan view of the organic film forming module 100, and FIGS. 6B and 6C illustrate organic film forming modules 100_C1 and 100_C2 whose structures are modified from that of FIG. 6A. FIG. 6D illustrates an example of a head 110 of the organic film forming module 100_C2 shown in FIG. 6C. Hereinafter, some exemplary embodiments will be described with reference to FIGS. 6A, 6B, 6C, 6D, 7A, and 7B. For concise description, an element previously described with reference to FIGS. 1, 2, 3, 4, and 5 may be identified by a similar or identical reference number without repeating a similar or identical description thereof.

As shown in FIG. 6A, the organic film forming module 100 may include a plurality of heads 110 and a surrounding portion 120. The surrounding portion 120 may be configured to allow that the heads 110 to be coupled to each other thereby forming a single body. A control unit (not shown) may be provided in the surrounding portion 120. The control unit may be configured to control motions of the heads 110. The surrounding portion 120 may be physically and electrically connected to the heads 110.

As shown in FIG. 6A, the organic film forming module 100 may include the heads 110, which are arranged in the second direction D2 and parallel to each other. A first column heads 110a which arrays in the second direction D2 and a second column heads 110b which arrays in the second direction D2 are shown in FIGS. 6A and 6B for convenience in description. The first column heads 110a and the second column heads 110b do not overlap each other in the first direction. In FIG. 6A, the second column heads 110b respectively apart from corresponding first column heads 110a by a first gap AP in the second direction D2. And in FIG. 6B, the second column heads 110b respectively apart from corresponding first column heads 110a by a second gap AP1 greater than the first gap AP in the second direction D2.

Motions of the heads 110 may be controlled independently for each of the heads 110. The organic film forming module 100 may be configured to control the motions of the heads 110, and this may make it possible to adjust the alignment accuracy of the ink pattern.

As shown in FIG. 6B, the adjustment of the positions of the heads 110 may be achieved by a translational motion R4. The organic film forming module 100_C1 may include the heads 110, which are spaced apart from each other by the second gap AP1 in the second direction D2.

In certain exemplary embodiments, as shown in FIG. 6C, the adjustment of the positions of the heads 110 may be achieved by a rotational motion. The organic film forming module 100_C2 may include the heads 110, which are arranged to extend in a direction that is inclined to the first and second directions D1 and D2.

Referring to FIG. 6D, the head 110 may include a plurality of nozzles 111 and a surrounding portion 112. The nozzles 111 may be formed to be inserted into the surrounding portion 112. The surrounding portion 112 may be provided to combine the nozzles 111, which are spaced apart from each other, to the head 110. Accordingly, motions of the nozzles 111 may be simultaneously controlled by controlling the motion of the head 110.

The head 110 may be tilted with respect to a first imaginary axis VX1, which extends parallel to the first direction D1, and a second imaginary axis VX2, which extends parallel to the second direction D2; for example, the head 110 may be tilted at an angle θ with respect to the second imaginary axis VX2. The head 110 may be rotated about a point of intersection of the first and second imaginary axes VX1 and VX2. Thus, the nozzles 111 may be configured to be movable in both of the first and second directions D1 and D2.

Since the organic film forming module 100 according to some exemplary embodiments is configured to control the motion of the heads 110, the nozzles 111 constituting the heads 110 may be designed to be arranged at various positions. Accordingly, the organic film forming module 100 may be used to realize various ink pattern arrangements through the translational and rotational motions of the heads 110.

For convenience in illustration, FIGS. 7A and 7B illustrate heads 110_S1 and 110_S2, each of which includes nozzles 111 arranged in a specific direction. Referring to FIG. 7A, the head 110_S1 may be aligned to extend in the second direction D2. In other words, the nozzles 111 may be arranged to be spaced apart from each other in the second direction D2. The head 110_S1 may correspond to the heads 110 shown in FIGS. 6A and 6B. Here, the two nozzles 111 may be provided to be spaced apart from each other by a predetermined space SP1, when measured in the second direction D2.

Referring to FIG. 7B, the head 110_S2 may be aligned to extend in a direction that is inclined at an angle to the first and second directions D1 and D2. In other words, the nozzles 111 may be arranged to be spaced apart from each other in the direction that is inclined with respect to the first and second directions D1 and D2. Here, a space SP2 between the two nozzles 111 measured in the second direction D2 may be less than the space SP1 of FIG. 7A. According to some exemplary embodiments, the space between the nozzles 111 in the second direction D2 may be adjusted through the rotational motion of the head 110_S2, and thus, it may be possible to easily control a space between the ink patterns.

Figure 8:
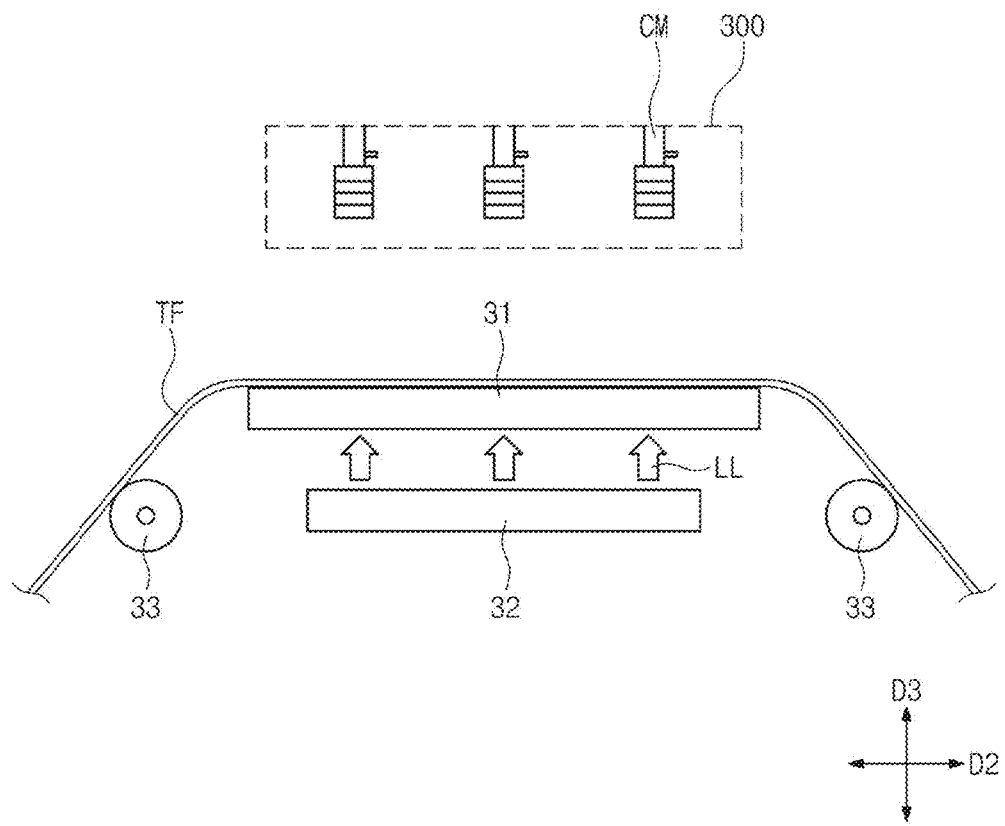
FIG. 8 is a sectional view schematically illustrating a portion of a display panel manufacturing system according to some exemplary embodiments.
Figure 9:
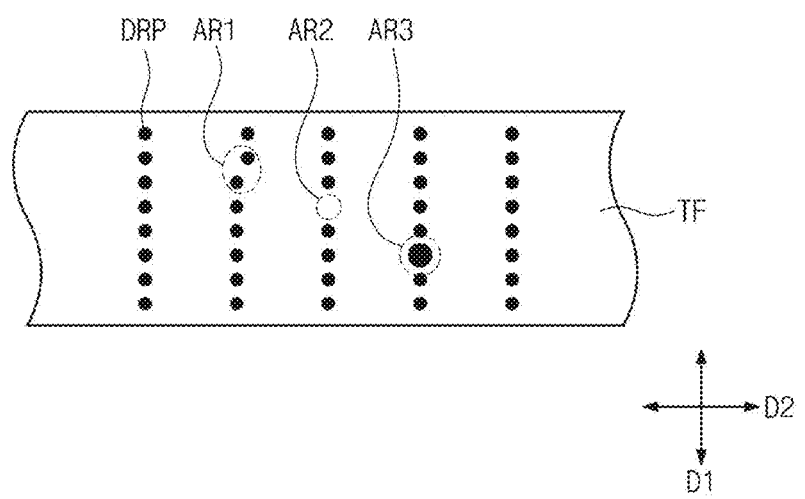
FIG. 9 is a plan view illustrating a portion of a test substrate.

FIG. 8 is a sectional view schematically illustrating a portion of a display panel manufacturing system according to some exemplary embodiments. FIG. 9 is a plan view illustrating a portion of a test substrate. For convenience in illustration, some elements are not illustrated in FIG. 8. The pattern inspection step S310 (e.g., see FIG. 1) is illustrated in FIG. 8, and a portion of the test substrate TF provided in the pattern inspection step S310 is illustrated in FIG. 9. Hereinafter, some exemplary embodiments will be described with reference to FIGS. 8 and 9. For concise description, elements previously described with reference to FIGS. 1 to 7B may be identified by a similar or identical reference number without repeating a similar description thereof.

As described above, in the pattern inspection step S310, the test substrate provider 30 (e.g., see FIG. 2) may be configured to provide the test substrate TF including the ink patterns, which are formed using the organic film forming module 100 (e.g., see FIG. 2), to the pattern inspection module 300 (e.g., see FIG. 2). FIG. 7 illustrates a process of inspecting the ink patterns formed on the test substrate TF using the pattern inspection module 300.

As shown in FIG. 8, the test substrate provider 30 may include a plurality of components. For example, the test substrate provider 30 may include a stage 31, a light source 32, and a roller 33. The stage 31 may be configured to allow the test substrate TF to be laid thereon. A portion placed on the stage 31 may be provided to various modules.

Although not shown, the stage 31 may further include a vacuum device, which is configured to hold the test substrate TF. Here, the test substrate TF may be in close contact with a surface of the stage 31 without any gap therebetween, thereby proving a flat top surface, and it may be possible to prevent a change in position of the test substrate TF with respect to the stage 31, which may be caused by the motion of the test substrate provider 30.

The light source 32 may be provided below the test substrate TF and may be used to provide light LL to the test substrate TF. The light LL may irradiate a rear surface of the test substrate TF, thereby improving visibility of ink patterns formed on the test substrate TF.

The roller 33 may be configured to coil or uncoil the test substrate TF. In the case where the test substrate TF is provided in the form of a flexible film, the test substrate TF may be uncoiled from the roller 33 and may be provided to the stage 31 or may be coiled around the roller 33 after the pattern inspection step S310. Accordingly, the test substrate TF may be continuously provided in the display panel manufacturing system.

The pattern inspection module 300 may be configured to inspect a plurality of ink patterns DRP (hereinafter, first ink patterns) formed on the test substrate TF. For example, the pattern inspection module 300 may include the imaging module 310, which is used to monitor the alignment accuracy and the shape of the first ink patterns DRP.

Referring to FIG. 9, the first ink patterns DRP may be arranged to form a plurality of columns, which extend in the first direction D1 and are spaced apart from each other in the second direction D2. The first direction D1 may be parallel to the motion direction of the substrate BP (e.g., see FIG. 2) and may correspond to the moving path of the test substrate provider 30.

Here, the test substrate TF may include a first region AR1, in which the first ink patterns DRP are misaligned to each other in the first direction D1. For example, the first ink patterns DRP in the first region AR1 may not be aligned to each other in the first direction D1.

In certain exemplary embodiments, the test substrate TF may include a second region AR2, in which an ink pattern is not formed. For example, the second region AR2 may be a region without any ink pattern. Thus, the test substrate TF may include an empty space such as the second region AR2.

In certain exemplary embodiments, the test substrate TF may include a third region AR3, in which a relatively large ink pattern is formed. For example, the first ink pattern DRP in the third region AR3 may be formed to have a relatively large area, compared with other ink patterns adjacent thereto.

The imaging module 310 according to some exemplary embodiments may detect an ink pattern, which may be formed in the first region AR1, the second region AR2, or the third region AR3, through inspection of the first ink patterns DRP. The presence/absence and positions of the first, second, and third regions AR1, AR2, and AR3 may be output as the pattern inspection result data and may be used to adjust positions of the heads 110 of the organic film forming module 100. According to some exemplary embodiments, the display panel manufacturing system may be configured to perform a pattern inspection, in which the test substrate TF is used, in real time during the organic pattern forming step S200. In addition, by inspecting the first ink patterns DRP formed on the test substrate TF, it may be possible to determine whether there is a failure of the heads 110 and to correct such a failure in real time. Thus, it may be possible to reduce process time and cost in a process of manufacturing a display panel.

Figure 10A:
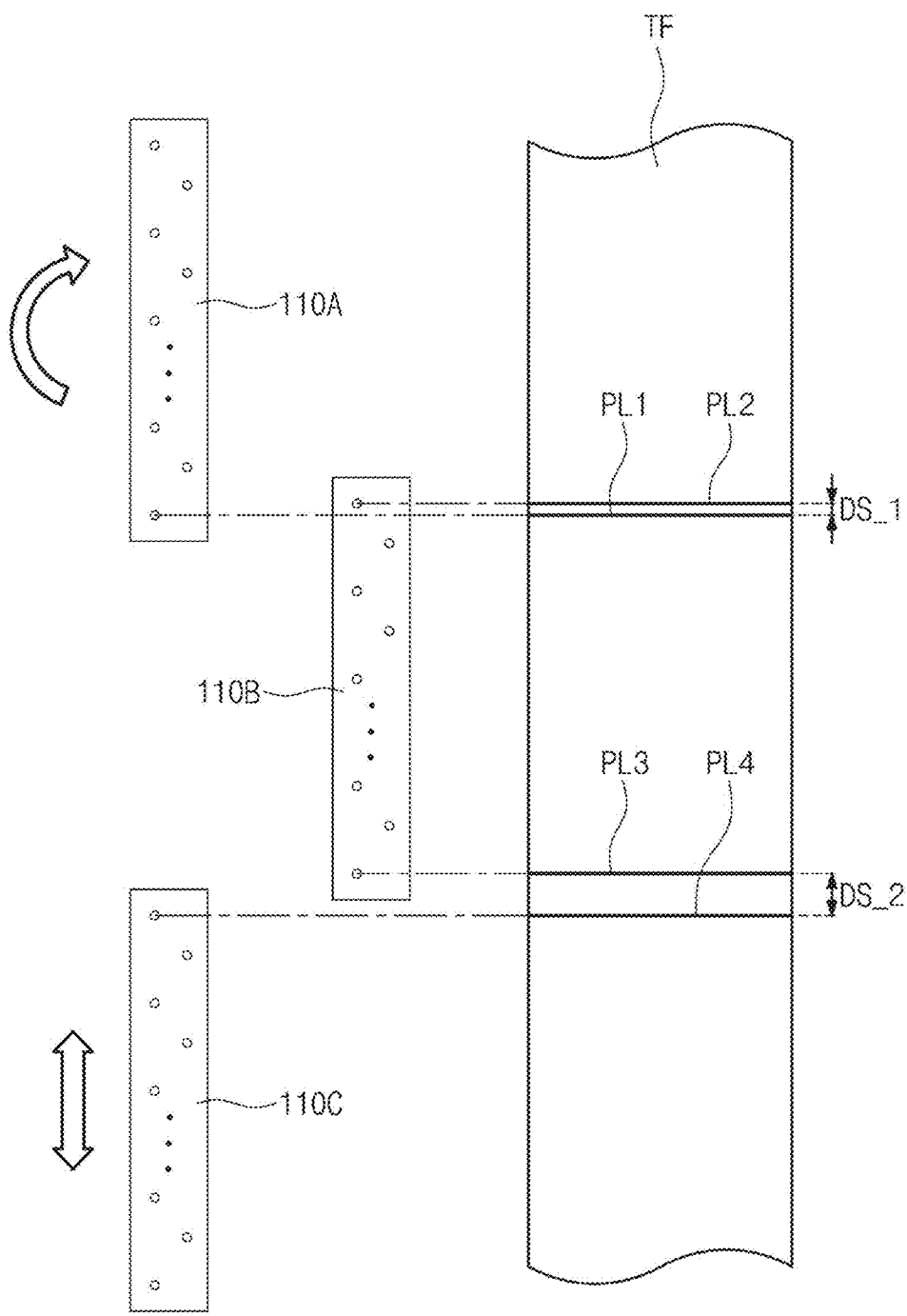
FIGS. 10A and 10B are plan views schematically illustrating a portion of a display panel manufacturing system according to some exemplary embodiments.
Figure 10B:
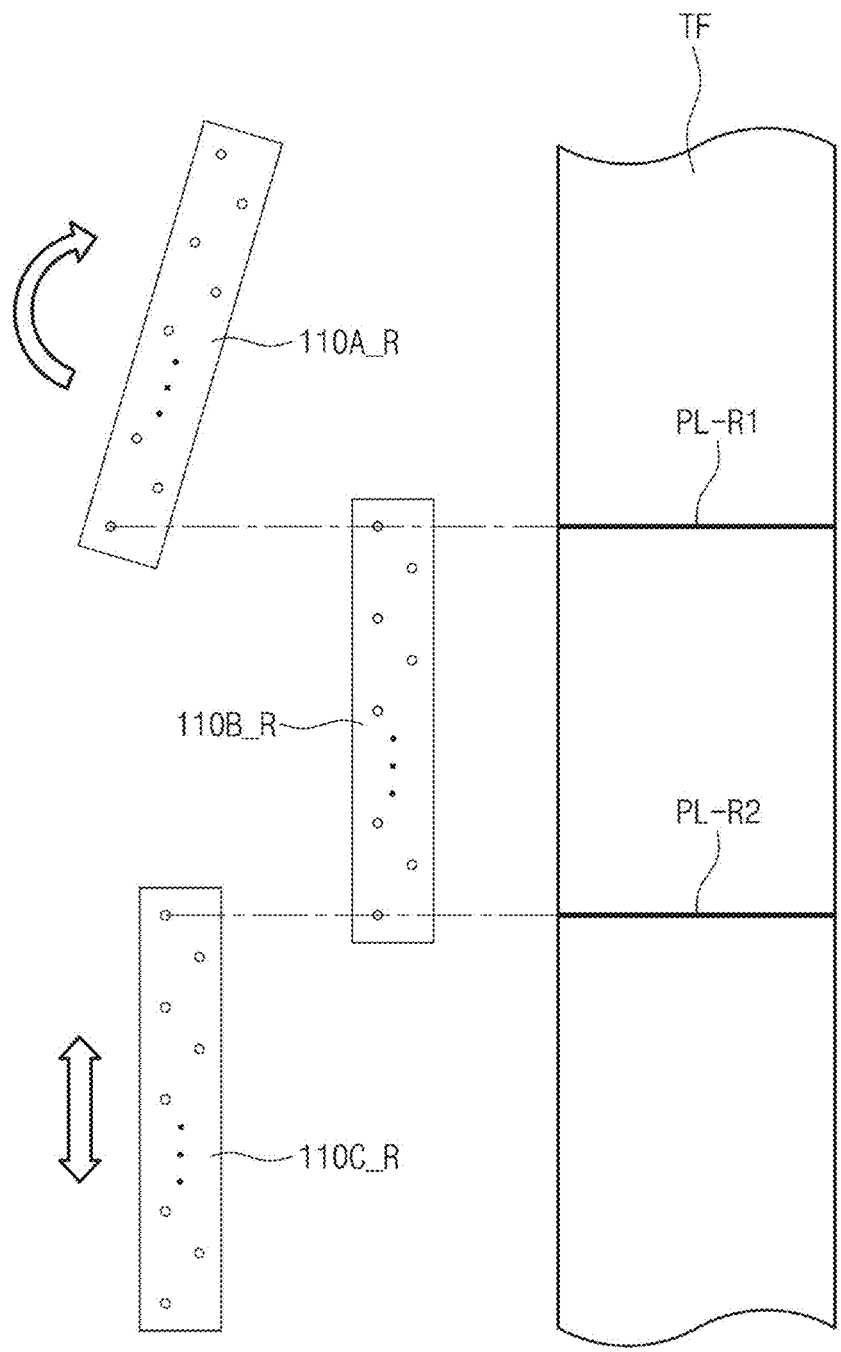

FIGS. 10A and 10B are plan views schematically illustrating a portion of a display panel manufacturing system according to some exemplary embodiments. Three of the heads and the test substrate TF are illustrated in FIGS. 10A and 10B. Hereinafter, a display panel manufacturing system according to some exemplary embodiments will be described with reference to FIGS. 10A and 10B.

FIG. 10A exemplarily illustrates some of ink patterns, which are formed on the test substrate TF by three heads 110A, 110B, and 110C. For example, a first pattern PL1 may be formed by a nozzle, which is included in the first head 110A and is positioned most adjacent to the second head 110B, a second pattern PL2 may be formed by a nozzle, which is included in the second head 110B and is positioned most adjacent to the first head 110A, a third pattern PL3 may be formed by a nozzle, which is included in the second head 110B and is positioned most adjacent to the third head 110C, and a fourth pattern PL4 may be formed by a nozzle, which is included in the third head 110C and is positioned most adjacent to the second head 110B.

The first pattern PL1 and the second pattern PL2 may be formed to be spaced apart from each other by a first gap DS_1. The third pattern PL3 and the fourth pattern PL4 may be formed to be spaced apart from each other by a second gap DS_2. In other words, at a region, in which the first head 110A and the second head 110B are positioned adjacent to each other, the ink pattern formed by the first head 110A may be misaligned comparing with the ink pattern formed by the second head 110B. Similarly, at a region, in which the second head 110B and the third head 110C are positioned adjacent to each other, the ink pattern formed by the second head 110B may be misaligned comparing with the ink pattern formed by the third head 110C.

In the case where the heads are aligned to each other, patterns formed by two adjacent nozzles will be formed along the same or single line. The nozzles in each of the heads 110A, 110B, and 110C may be spaced apart from each other by the same space, and thus, if adjacent nozzles are arranged along the same or single line, all of the ink patterns formed by the heads 110A, 110B, and 110C may be sequentially aligned.

In the case where the three heads 110A, 110B, and 110C are moved in the arrow direction to adjust positions of the three heads 110A, 110B, and 110C, two adjustment patterns (e.g., a first adjustment pattern PL-R1 and a second adjustment pattern PL-R2) may be formed on the test substrate TF, as shown in FIG. 10B.

When considering the alignment accuracy between the first head 110A and the second head 110B on the basis of the first pattern PL1 and the second pattern PL2, the space between the first head 110A and the second head 110B may result from a small misalignment in that the first pattern PL1 is formed to be shifted toward the second head 110B, compared with the second pattern PL2. Based on the result data, the first head 110A may be rotated in the arrow direction, thereby forming an adjusted first head 110A_R. Accordingly, the first gap DS_1 between the first pattern PL1 and the second pattern PL2 may be reduced, and both of the first pattern PL1 and the second pattern PL2 may coincide with the first adjustment pattern PL-R1.

When considering the alignment accuracy between the second head 110B and the third head 110C on the basis of the third pattern PL3 and the fourth pattern PL4, the space between the second head 110B and the third head 110C may result from a large misalignment. Based on the result data, the third head 110C may be linearly moved in the arrow direction, thereby forming an adjusted third head 110C_R. Accordingly, the second gap DS_2 between the third pattern PL3 and the fourth pattern PL4 may be reduced, and both of the third pattern PL3 and the fourth pattern PL4 may coincide with a second adjustment pattern PL-R2.

According to some exemplary embodiments, on the basis of the pattern inspection result obtained from the ink patterns on the test substrate TF, the heads 110A, 110B, and 110C may be adjusted to form the aligned heads 110A_R, 110B_R, and 110C_R. The adjustment of the positions of the heads may be achieved by a rotational motion and a translational motion and may be controlled independently for each of the heads. In the present exemplary embodiment, for convenience in illustration, the position of the second head 110B is illustrated to be fixed, but the inventive concept is not limited thereto. For example, all of the positions of the three heads may be adjusted.

Figure 11A:
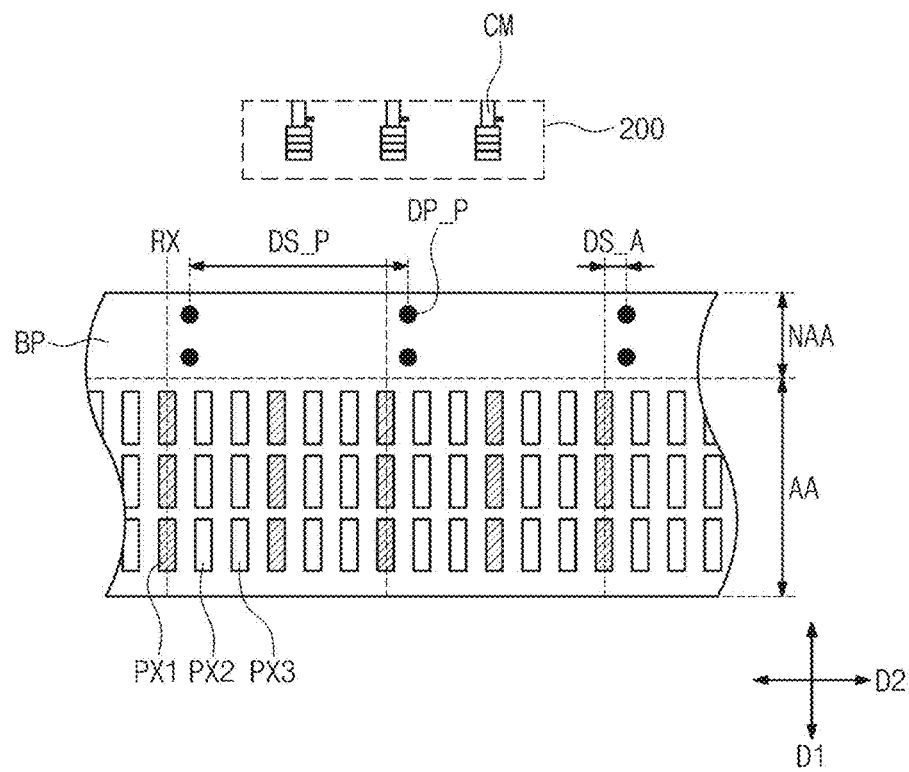
FIGS. 11A and 11B are diagrams illustrating some steps in a method of manufacturing a display panel according to some exemplary embodiments.
Figure 11B:
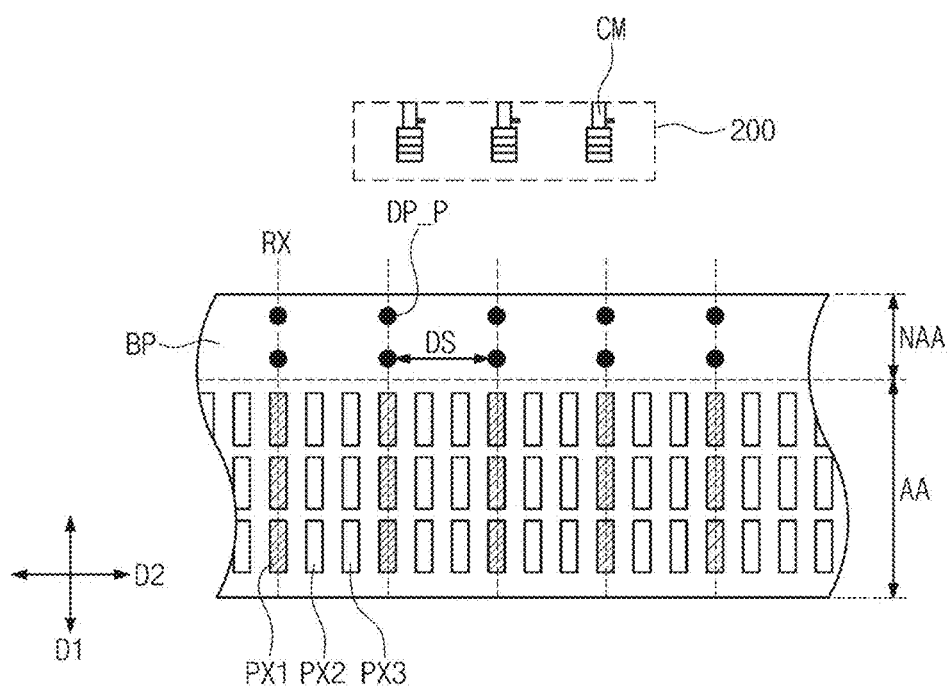

FIGS. 11A and 11B are diagrams illustrating some steps in a method of manufacturing a display panel according to some exemplary embodiments. FIGS. 11A and 11B illustrate the substrate BP and the offset inspection module 200 in the offset inspection step S320 (e.g., see FIG. 1). Hereinafter, some exemplary embodiments will be described with reference to FIGS. 11A and 11B. For concise description, an element previously described with reference to FIGS. 1 to 10B may be identified by a similar or identical reference number without repeating a similar description thereof.

The active region AA of the substrate BP may include a plurality of pixel regions PX1, PX2, and PX3. Each of the pixel regions PX1, PX2, and PX3 may correspond to the opening OPP of FIG. 5. As shown, a plurality of ink patterns DP_P (hereinafter, second ink patterns) may be formed on the peripheral region NAA of the substrate BP. Each of the second ink patterns DP_P may correspond to the inspection pattern ISP of FIG. 5.

In the present exemplary embodiment, the second ink patterns DP_P may correspond to ink patterns filling the first pixel region PX1. Thus, among the pixel regions PX1, PX2, and PX3, the first pixel region PX is illustrated with a hatching pattern.

As shown in FIG. 11A, the second ink patterns DP_P may be arranged to be spaced apart from each other by a predetermined space DS_P in the second direction D2. In FIG. 11A, the second ink patterns DP_P is shown, the second ink patterns DP_P may be formed to be spaced apart from a reference line RX passing through the first pixel region PX1, by a predetermined gap DS_A.

Also, there may be a region in which the second ink pattern DP_P is not provided. In this case, the space DS_P between the second ink patterns DP_P may be larger than the space between the first pixel regions PX1. In other words, as shown in FIG. 11A, misalignment may occur between the second ink patterns DP_P and the substrate BP.

The offset inspection module 200 may inspect the second ink patterns DP_P while moving a plurality of camera modules CM in the second direction D2. Here, the misalignment between the second ink patterns DP_P and the substrate BP may be detected, and the offset inspection result data containing information on the misalignment may be produced.

FIG. 11B illustrates the second ink patterns DP_P, which are formed using the organic film forming module 100 (e.g., see FIG. 2) aligned in consideration of the offset inspection result data. As shown in FIG. 11B, the second ink patterns DP_P may be aligned and arranged along the reference lines RX. Also, the second ink patterns DP_P may be formed in such a way that the space DS therebetween is substantially equal to the space between the first pixel regions PX1.

The offset inspection module 200 may be configured to inspect the second ink patterns DP_P and to produce offset inspection result data, in which information on alignment between the second ink patterns DP_P and the substrate BP is contained. If the offset inspection result data is reflected, the organic film forming module 100 may stop the alignment adjustment, based on the offset inspection result, and may form ink patterns on the active region AA to finish a step of forming organic patterns on the pixel regions PX1, PX2, and PX3.

Although not shown, the offset inspection module 200 may be configured to inspect a shape or size of the second ink pattern DP_P and to produce offset inspection result data, in which information regarding this is contained. Such offset inspection result data may be reflected to the organic film forming module 100 and may be used to selectively find a failed head and transfer it to the droplet inspection module 400 (e.g., see FIG. 2). That is, the droplet inspection step S330 (e.g., see FIG. 1) may be performed during the offset inspection step S320.

In the display panel manufacturing system according to some exemplary embodiments, the organic pattern forming step and the inspection step may be performed in conjunction with each other, and this may make it possible to reflect the inspection result of the ink pattern in real time and to form organic patterns with improved quality. Furthermore, since the organic pattern forming step and the inspection step are performed simultaneously, it may be possible to reduce process time and cost in a process of manufacturing a display panel.

Figure 12:
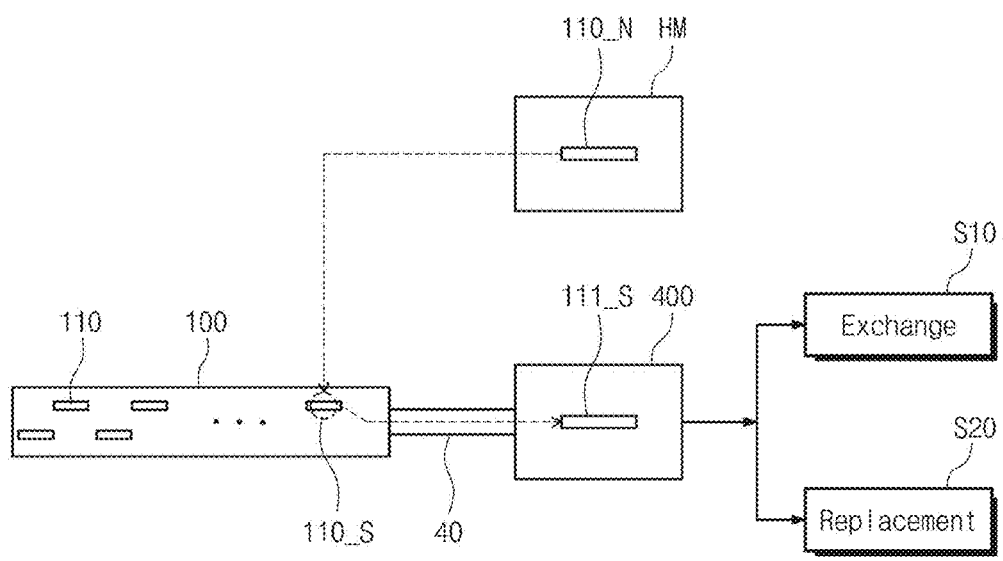
FIG. 12 is a diagram illustrating some steps of manufacturing a display panel according to some exemplary embodiments.
Figure 13:
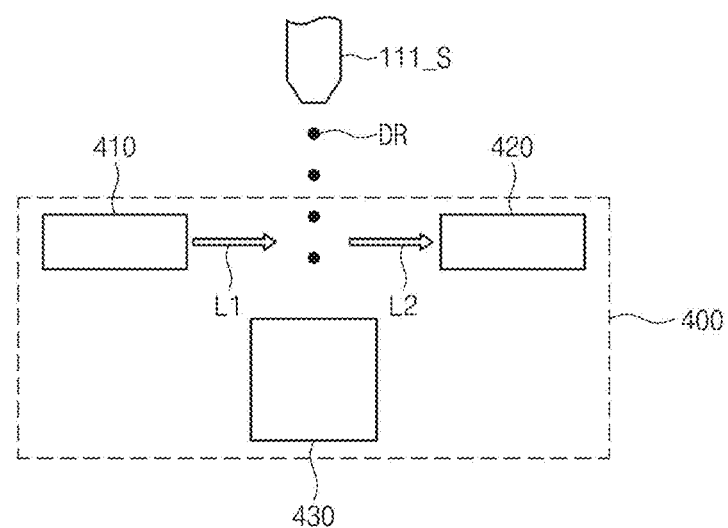
FIG. 13 is a diagram illustrating a portion of a structure shown in FIG. 12.

FIG. 12 is a diagram illustrating some steps of manufacturing a display panel according to some exemplary embodiments. FIG. 13 is a diagram illustrating a portion of a structure shown in FIG. 12. FIG. 12 schematically illustrates the droplet inspection step S330 (e.g., see FIG. 1), and FIG. 13 schematically illustrates a cross section of the droplet inspection module 400 shown in FIG. 12. Hereinafter, some exemplary embodiments will be described with reference to FIGS. 12 and 13.

As shown in FIG. 12, one (e.g., a head 110_S) of the heads 110 in the organic film forming module 100 may be selected and may be moved to the droplet inspection module 400. Here, the selected head 110_S may be moved to the droplet inspection module 400 through the gantry part 40, but the inventive concept is not limited to the example. For example, the selected head 110_S may be moved to the droplet inspection module 400 through other path.

The selected head 110_S may be selected, based on data produced in at least one of the pattern inspection step S310 and the offset inspection step S320, as described above. The droplet inspection module 400 may be configured to inspect an ink to be dropped from the selected head 110_S. Here, the droplet inspection module 400 may be configured to inspect an ink to be dropped from each of the nozzles of the selected head 110_S. For convenience in illustration, one (e.g., a nozzle 111_S) of the nozzles of the selected head 110_S is exemplarily illustrated in FIG. 13.

As shown in FIG. 13, the droplet inspection module 400 may be configured to examine condition of the nozzle 111_S using an ink DR dropping from the nozzle 111_S. The droplet inspection module 400 may include a light emitting unit 410, a light receiving unit 420, and an ink collecting unit 430.

The light emitting unit 410 may be configured to emit light L1 toward the ink DR. The light L1, which is incident into the ink DR, may be scattered or transmitted to form light L2 propagating toward the light receiving unit 420. The light L2 may contain information on distribution of the ink DR.

In the present exemplary embodiment, the light emitting unit 410 may include a laser emitting device. The light receiving unit 420 may include a photodetector. In the present exemplary embodiment, since the distribution of the ink DR is measured using a laser beam with high directivity, the use of the droplet inspection module 400 may make it possible to produce highly-accurate droplet distribution data.

The ink collecting unit 430 may be configured to contain the ink DR dropping from the nozzle 111_S. The ink DR may be contained in the ink collecting unit 430, regardless of whether it is irradiated with the light L1 or not.

Referring back to FIG. 13, the droplet inspection module 400 may be configured to examine all of the nozzles 111_S of the selected head 110_S and to produce the droplet inspection result data therefrom. The droplet inspection result data may be produced to contain information on ink distribution of the nozzles 111_S of the selected head 110_S and on whether ink is ejected from the nozzles 111_S.

The droplet inspection module 400 may be configured to perform an adjustment step S10 or a replacement step S20 on the selected head 110_S, on the basis of the droplet inspection result data. In the case where the adjustment step S10 is performed on the selected head 110_S, an amount of the ink to be dropped from the nozzles 111_S may be controlled to realize a desired ink distribution, and then, the adjusted head may be returned back to the organic film forming module 100. In the case where the replacement step S20 is performed on the selected head 110_S, a new head 110_N may be moved from a head storage HM to the organic film forming module 100, and then, the selected head 110_S may be replaced with the new head 110_N.

According to some exemplary embodiments, the droplet inspection module 400 may be configured to selectively perform a droplet inspection process on the selected head 110_S, and thus, it may be possible to selectively perform the droplet inspection process on a failed head. Since the droplet inspection process on the selected head 110_S is performed in real time during the pattern inspection step S310 or the offset inspection step S320, there is no need to perform an additional scanning process for selecting a head. In addition, by performing the adjustment or replacement step S10 or S20 based on the droplet inspection result data produced by the droplet inspection module 400, it may be possible to correct a failed head to a normal head and to easily perform the droplet inspection process even when the organic film forming module 100 is being operated. Accordingly, it may be possible to reduce a process time taken to perform the droplet inspection process and consequently to reduce the total process time.

Figure 14B:
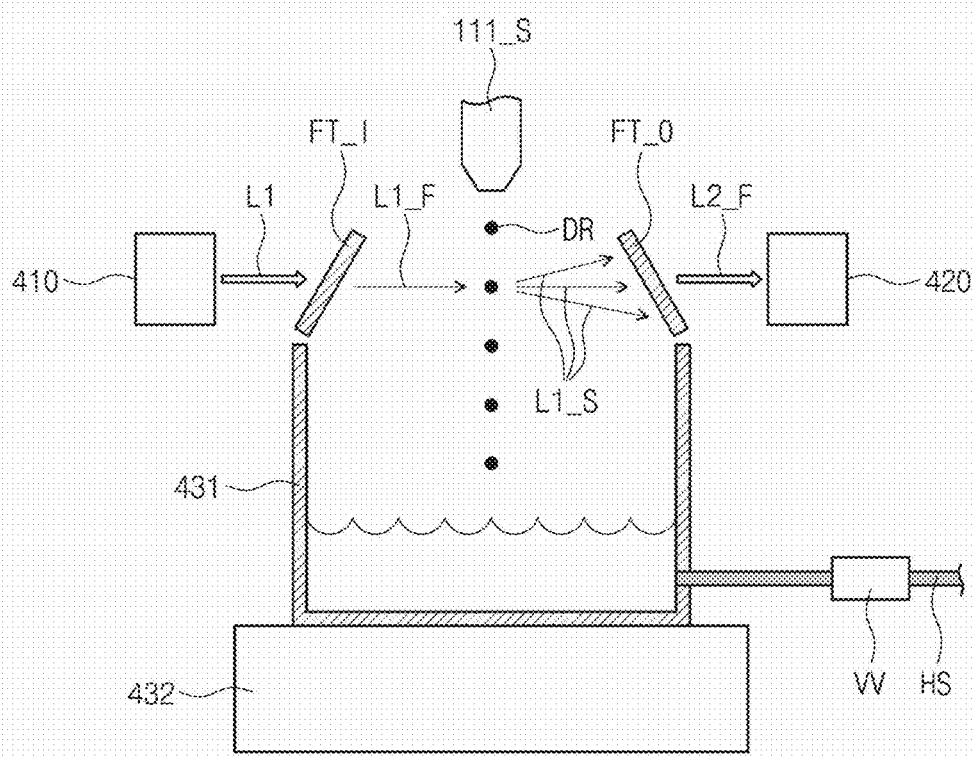

FIGS. 14A and 14B are cross-sectional views, each illustrating a portion of a display panel manufacturing system according to some exemplary embodiments. The ink collecting unit 430 and the nozzle 111_S are schematically illustrated in FIG. 14A, and the droplet inspection module 400 and the nozzle 111_S are schematically illustrated in FIG. 14B. Hereinafter, some exemplary embodiments will be described with reference to FIGS. 14A and 14B.

As shown in FIG. 14A, the ink collecting unit 430 may include an ink container 431, an electronic balance device 432, and a suction device 433.

the ink container 431 may provide a space for containing the ink DR to be dropped from the nozzle 111_S. The space in the ink container 431 may be filled with the ink DR. If necessary, the ink DR filling the ink container 431 may be emptied to the outside through a hose HS, which is connected to the ink container 431. In certain exemplary embodiments a valve VV may be provided on the hose HS to control a flow rate of the ink DR flowing through the hose HS.

The electronic balance device 432 may be provided below the ink container 431. The electronic balance device 432 may be configured to measure a weight of the ink DR filling the ink container 431. The electronic balance device 432 may be used to continuously monitor a weight of the ink DR to be dropped into the ink container 431. The weight of the ink DR measured by the electronic balance device 432, along with information on distribution of the ink DR received through the light receiving unit 420, may affect a process of producing the droplet inspection result data.

The suction device 433 may be provided between the nozzle 111_S and the ink container 431. The suction device 433 may be provided near a dropping path of the ink DR, which is dropped from the nozzle 111_S, and may be used to collect a portion of the dropping ink DR. Accordingly, it may be possible to stably collect a portion of the dropping ink DR departed from a predetermined path and consequently to prevent the ink DR from being leaked to the outside of the ink container 431.

Referring to FIG. 14B, the droplet inspection module 400 may further include a plurality of optical filters FT_I and FT_O. The optical filters FT_I and FT_O are provided to face each other with the nozzle 111_S interposed therebetween.

The first filter FT_I may be provided between the light emitting unit 410 and the dropping ink DR. The first filter FT_I may be used to perform a filtering process on the light L1 emitted from the light emitting unit 410. For example, the first filter FT_I may be configured to provide light L1_F, which is controlled to have improved directivity and a uniform wavelength, to the ink DR.

The second filter FT_O may be provided between the dropping ink DR and the light receiving unit 420. The second filter FT_O may be configured to perform a filtering process on light L1_S, which is scattered by the ink DR or is transmitted through the ink DR, and thereby to generate light L2_F propagating in a direction toward the light receiving unit 420.

Accordingly, it may be possible to stably maintain quality of light, which is used to measure distribution of the ink DR, and to stably maintain an amount of light to be incident into the light receiving unit 420. This may make it possible to improve reliability in the droplet inspection process.

According to some exemplary embodiments, the droplet inspection module including various components may be used to stably measure distribution of the ink DR and to obtain highly accurate droplet inspection result. In addition, the droplet inspection process may be selectively performed on only a selected head and may be performed simultaneously with the organic pattern forming step. Thus, it may be possible to reduce process time and cost in a process of manufacturing a display panel.

Figure 15:
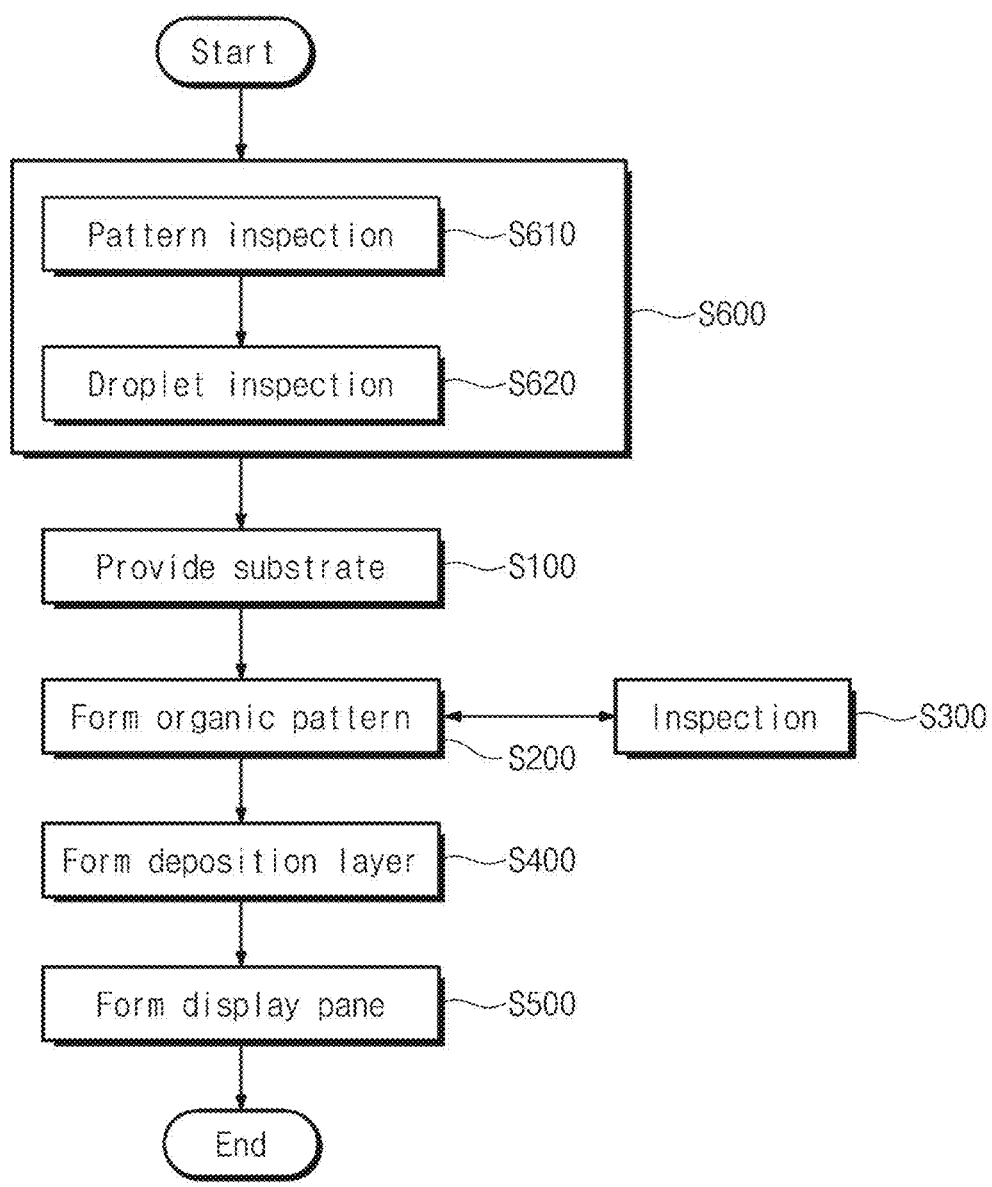
FIG. 15 is a flow chart illustrating a method of manufacturing a display panel according to some exemplary embodiments.

FIG. 15 is a flow chart illustrating a method of manufacturing a display panel according to some exemplary embodiments. In a manufacturing method of FIG. 15, an initial inspection step S600 may be further performed, and except for the initial inspection step S600, the method of FIG. 15 may be performed in the same manner as that of FIG. 1. Thus, the elements and features of this example that are similar to those previously shown and described will not be described in much further detail, for the sake of brevity.

As shown in FIG. 15, the method of manufacturing a display panel may further include the initial inspection step S600. The initial inspection step S600 may be performed before the substrate providing step S100.

The initial inspection step S600 may include a pattern inspection step S610 and a droplet inspection step S620. The pattern inspection step S610 may be performed in the same manner as the pattern inspection step S310 of the inspection step S300 (e.g., see FIG. 1). Similarly, the droplet inspection step S620 may be performed in the same manner as the droplet inspection step S330 of the inspection step S300 (e.g., see FIG. 1).

In some exemplary embodiments, since the initial inspection step S600 is further performed before the substrate providing step S100, it may be possible to more uniformly control an initial alignment accuracy of the substrate and initial values of the heads of the organic film forming module 100 (e.g., see FIG. 2). By virtue of the initial inspection step S600, it may be possible to reduce the time taken to perform the inspection step S300.

The display panel manufacturing system 1000 (e.g., see FIG. 2) according to some exemplary embodiments may be used for the initial inspection step S600. According to some exemplary embodiments, a single display panel manufacturing system may be used to perform not only the organic pattern forming step S200 but also a step of inspecting an ink pattern before the organic pattern forming step S200, and thus, it may be possible to simplify the manufacturing process and to reduce cost for the manufacturing process.

According to some exemplary embodiments, an inspection step for examining whether there is ink misalignment is performed during an inkjet process for forming an organic pattern. Accordingly, it may be possible to reduce process time and cost in a process of manufacturing a display panel.

According to some exemplary embodiments, during an organic pattern forming step, an ink dropping adjustment may be easily performed in real time, and a droplet inspection may be selectively performed on a failed head. Accordingly, it may be possible to simplify a manufacturing process and to improve reliability of a display panel.

While exemplary embodiments have been particularly shown and described, it will be understood by one of ordinary skill in the art that variations in form and detail may be made therein without departing from the spirit and scope of the attached claims.

What is claimed is:
1. A display panel manufacturing system, comprising:
   a substrate providing module configured to provide a substrate comprising an active region, thin-film transistors disposed on the active region, and a peripheral region adjacent to the active region;
   a test substrate providing module configured to provide a test substrate;

an organic film forming module configured to form an ink pattern on each of the substrate and the test substrate, the organic film forming module comprising a plurality of heads, each of the plurality of heads configured to drop an ink;

an offset inspection module configured to inspect the ink pattern on the substrate;

a pattern inspection module configured to inspect the ink pattern on the test substrate; and a droplet inspection module configured to inspect an ink, the ink dropped from a selected head from the plurality of heads, wherein the organic film forming module, the offset inspection module, and the droplet inspection module are configured to move together.

2. The system of claim 1, wherein the organic film forming module is configured to form first ink patterns on the test substrate, and the pattern inspection module is configured to inspect the first ink patterns and to adjust positions of the plurality of heads.

3. The system of claim 2, wherein the organic film forming module is configured to form second ink patterns on the substrate, and the offset inspection module is configured to inspect alignment accuracy between patterns, and to adjust positions of the plurality of heads, the patterns respectively formed on the active region and the peripheral region and selected from the second ink patterns.

4. The system of claim 3, wherein the second ink patterns are formed on the active region and the peripheral region.

5. The system of claim 3, wherein the plurality of heads are configured to move in a direction perpendicular to a motion direction of the substrate by the offset inspection module; and to move and rotate in a direction perpendicular to the motion direction of the substrate by the pattern inspection module.

6. The system of claim 3, wherein the selected head is selected from the plurality of heads, when the first ink patterns or the second ink patterns are being inspected.

7. The system of claim 6, wherein each of the heads comprises a plurality of nozzles, and at least one of the nozzles of the selected head does not eject the ink or forms an ink pattern whose size is different from that of a reference ink pattern.

8. The system of claim 1, wherein the droplet inspection module comprises a laser irradiation device and an electronic balance device, and the laser irradiation device is provided between the electronic balance device and the selected head and is configured to inspect the ink, the ink provided from the selected head to the electronic balance device.

9. The system of claim 8, wherein the droplet inspection module further comprises a filter, the laser irradiation device comprises a laser irradiation part, the laser irradiation part is configured to irradiate the ink with a laser beam, and a laser receiving part, the laser receiving part is configured to receive the laser beam emitted from the ink, and the filter is configured to control an intensity of the laser beam, which is incident from the laser irradiation part, and to control directivity of the laser beam, which is emitted from the ink.

10. The system of claim 9, wherein the filter comprises a diffraction slit.

11. The system of claim 8, wherein the droplet inspection module further comprises an ink suction device, and the ink suction device is disposed between the electronic balance device and the selected head, and the ink suction device is configured to suck an ink to be leaked to an outside of the electronic balance device.

* * * * *